United States Patent
Finley et al.

(10) Patent No.: US 11,980,415 B2
(45) Date of Patent: May 14, 2024

(54) ROBOTIC SURGERY

(71) Applicant: NuVasive, Inc., San Diego, CA (US)

(72) Inventors: Eric Finley, San Diego, CA (US);
Adrien Ponticorvo, San Diego, CA (US); Mike Serra, San Diego, CA (US); Christopher Nelsen, San Diego, CA (US); Robert German, San Diego, CA (US); Justin Doose, San Diego, CA (US); Danielle Richterkessing, San Diego, CA (US); Antonio Ubach, Tucson, AZ (US); John C. Love, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 133 days.

(21) Appl. No.: 17/537,651

(22) Filed: Nov. 30, 2021

(65) Prior Publication Data
US 2022/0183755 A1 Jun. 16, 2022

Related U.S. Application Data

(60) Provisional application No. 63/124,627, filed on Dec. 11, 2020.

(51) Int. Cl.
*A61B 18/22* (2006.01)
*A61B 18/00* (2006.01)
*A61B 18/20* (2006.01)
*A61B 34/20* (2016.01)

(52) U.S. Cl.
CPC .............. *A61B 18/22* (2013.01); *A61B 34/20* (2016.02); *A61B 2018/00339* (2013.01); *A61B 2018/00875* (2013.01); *A61B 2018/2035* (2013.01)

(58) Field of Classification Search
CPC .... A61B 18/22; A61B 34/20; A61B 2090/373
See application file for complete search history.

(56) References Cited

U.S. PATENT DOCUMENTS

| 5,211,164 | A  | 5/1993  | Allen      |
|-----------|----|---------|------------|
| 5,241,972 | A  | 9/1993  | Bonati     |
| 5,401,171 | A  | 3/1995  | Paghdiwala |
| 5,415,652 | A  | 5/1995  | Mueller    |
| 5,562,609 | A  | 10/1996 | Brumbach   |
| 5,782,823 | A  | 7/1998  | Mueller    |
| 6,361,531 | B1 | 3/2002  | Hissong    |

(Continued)

FOREIGN PATENT DOCUMENTS

| EP | 3117792 A1     | 1/2017 |
|----|----------------|--------|
| WO | 2020-127866 A1 | 6/2020 |

(Continued)

OTHER PUBLICATIONS

PCT Int'l Search Report and Written Opinion in Int'l Appln. PCT/US2021/062862, dated Apr. 7, 2022, 14 pages.

(Continued)

*Primary Examiner* — Michael W Kahelin
*Assistant Examiner* — Thien Jason Tran

(57) ABSTRACT

A laser or ultrasonic instrument is used to remove tissue during a surgery, such as to form one or more pilot holes in a vertebra or a window in bone. Where a laser is used, interrogative laser pulses can be used to obtain information, such as detecting depth or tissue type.

19 Claims, 14 Drawing Sheets

(56) References Cited

U.S. PATENT DOCUMENTS

| | | |
|---|---|---|
| 6,517,531 B2 | 2/2003 | Liu |
| 6,529,758 B2 | 3/2003 | Shahidi |
| 6,985,766 B2 | 1/2006 | Braun |
| 7,445,618 B2 | 11/2008 | Eggers |
| 7,887,567 B2 | 2/2011 | Shoham |
| 8,790,406 B1 | 7/2014 | Smith |
| 9,050,131 B2 | 6/2015 | Van Vorhis |
| 9,387,041 B2 | 7/2016 | Dahotre |
| 9,480,534 B2 | 11/2016 | Bowling |
| 9,510,771 B1 | 12/2016 | Finley |
| 9,649,342 B2 | 5/2017 | Flood |
| 9,820,818 B2 | 11/2017 | Malackowski |
| 10,092,741 B2 | 10/2018 | Darian |
| 10,267,624 B2 | 4/2019 | Breisacher |
| 10,470,788 B2 | 11/2019 | Sinelnikov |
| 10,588,614 B2 | 3/2020 | Gittings |
| 10,631,934 B2 | 4/2020 | Forstein |
| 10,716,643 B2 | 7/2020 | Justin |
| 2005/0222681 A1* | 10/2005 | Richley ............... A61F 2/446 623/908 |
| 2006/0293630 A1 | 12/2006 | Manna |
| 2007/0248136 A1 | 10/2007 | Leonardo |
| 2008/0015436 A1 | 1/2008 | Mikus |
| 2009/0126741 A1 | 5/2009 | Voic |
| 2009/0275933 A1* | 11/2009 | Zelickson ............ A61B 18/22 606/15 |
| 2011/0245819 A1 | 10/2011 | Nardini et al. |
| 2012/0197320 A1 | 8/2012 | Bereczki |
| 2012/0220992 A1 | 8/2012 | Bruno |
| 2013/0060146 A1* | 3/2013 | Yang .................. G01B 11/25 600/476 |
| 2014/0378999 A1 | 12/2014 | Crawford |
| 2015/0126984 A1 | 5/2015 | Boutoussov |
| 2015/0327930 A1 | 11/2015 | Bruno et al. |
| 2016/0135890 A1 | 5/2016 | Bruno |
| 2016/0135906 A1 | 5/2016 | Cattin |
| 2016/0166320 A1 | 6/2016 | Ciulla |
| 2017/0167702 A1 | 6/2017 | Mariampillai |
| 2017/0252109 A1 | 9/2017 | Yang |
| 2018/0008353 A1 | 1/2018 | Kostrzewski |
| 2018/0014890 A1* | 1/2018 | Stanton ............... A61B 90/39 |
| 2018/0078317 A1 | 3/2018 | Mariampillai |
| 2018/0214207 A1 | 8/2018 | Deibel |
| 2018/0256254 A1 | 9/2018 | Cattin |
| 2019/0005661 A1 | 1/2019 | Steinle |
| 2019/0094472 A1 | 3/2019 | Altshuler |
| 2019/0142515 A1 | 5/2019 | Dahotre |
| 2019/0159789 A1 | 5/2019 | Bruno et al. |
| 2019/0216559 A1 | 7/2019 | Krebs |
| 2019/0247055 A1 | 8/2019 | Nahum |
| 2019/0254772 A1 | 8/2019 | Leung |
| 2019/0269476 A1 | 9/2019 | Bowling |
| 2019/0298448 A1 | 10/2019 | Kerbage et al. |
| 2019/0307513 A1 | 10/2019 | Leung |
| 2019/0333253 A1 | 10/2019 | Mariampillai |
| 2019/0336004 A1 | 11/2019 | Mihailescu |
| 2019/0350658 A1 | 11/2019 | Yang |
| 2019/0365467 A1 | 12/2019 | Bruno |
| 2019/0374295 A1 | 12/2019 | Librot |
| 2020/0076151 A1 | 3/2020 | Bordenyuk |
| 2020/0078097 A1 | 3/2020 | Gregerson |
| 2020/0085509 A1 | 3/2020 | Roh |
| 2020/0100847 A1 | 4/2020 | Siegler |
| 2020/0197100 A1 | 6/2020 | Leung |
| 2020/0242830 A1 | 7/2020 | Bharadwaj |
| 2020/0246080 A1 | 8/2020 | Yang |
| 2020/0289211 A1 | 9/2020 | Leung |
| 2021/0052298 A1* | 2/2021 | Thommen .......... A61B 1/00128 |
| 2022/0378526 A1* | 12/2022 | Balicki ................ A61B 34/10 |
| 2023/0101192 A1* | 3/2023 | Shelton, IV ....... A61B 1/00193 600/109 |

FOREIGN PATENT DOCUMENTS

| | | |
|---|---|---|
| WO | 2020231880 | 11/2020 |
| WO | 2021062001 | 4/2021 |

OTHER PUBLICATIONS

Abbasi, H. et al., "Combined Nd:YAG and Er:YAG lasers for real-time closed-loop tissue-specific laser osteotomy", Biomedical Optics Express, Apr. 1, 2020, vol. 11, No. 4, pp. 1790-1807.

Rupprecht, S. et al., "Er:YAG laser osteotomy directed by sensor controlled systems", Journal of Cranio-Maxillofacial Surgery, 2003, vol. 31, No. 6, pp. 337-342.

Wikipedia, Laser Drilling (last edited Jun. 28, 2020).

Stern and Biscup, Invited Review and Commentary Lasers in Spine Surgery, Spine Line, pp. 17-23 (Sep.-Oct. 2009).

Radcliff et al, Lasers in Spine Surgery, Journal of the American Academy of Orthopaedic Surgeons: Sep. 1, 2019—vol. 27—Issue 17—p. 621-632 doi: 10.5435/JAAOS-D-18-00001.

Tatsui, Utilization of laser interstitial thermotherapy guided by real-time thermal MRI as an alternative to separation surgery in the management of spinal metastasis, J Neurosurg Spine 23:400-411 (2015).

Snyder et al, The Technological Development of Minimally Invasive Spine Surgery, BioMed Research Intl. vol. 2014 (May 21, 2014).

PCT International Preliminary Report on Patentability in Application PCT/US2021/062862, dated Jun. 16, 2022, 9 pages.

\* cited by examiner

500

```
┌─────────────────────────────────────────────────────────────────┐
│              EXPOSING A VERTEBRA OF A PATIENT 302               │
└─────────────────────────────────────────────────────────────────┘
                                │
                                ▼
┌─────────────────────────────────────────────────────────────────┐
│  DISPOSING A DISTAL END OF A LASER INSTRUMENT PROXIMATE THE     │
│                          VERTEBRA 304                           │
└─────────────────────────────────────────────────────────────────┘
                                │
                                ▼
┌─────────────────────────────────────────────────────────────────┐
│            CREATING A PILOT HOLE IN THE VERTEBRA 530            │
│                                                                 │
│  ┌───────────────────────────────────────────────────────────┐  │
│  │ ADVANCING THE LASER INSTRUMENT TOWARD THE VERTEBRA AFTER  │  │
│  │ REMOVING A FIRST AMOUNT OF TISSUE FROM THE VERTEBRA AND   │  │
│  │ BEFORE REMOVING A SECOND AMOUNT OF TISSUE FROM THE        │  │
│  │                      VERTEBRA 532                         │  │
│  └───────────────────────────────────────────────────────────┘  │
│                                                                 │
│  ┌───────────────────────────────────────────────────────────┐  │
│  │ REPEATEDLY CHANGING A DIRECTION OF LASER PULSES EMITTED   │  │
│  │            FROM THE LASER INSTRUMENT 534                  │  │
│  └───────────────────────────────────────────────────────────┘  │
└─────────────────────────────────────────────────────────────────┘
                                │
                                ▼
┌─────────────────────────────────────────────────────────────────┐
│  MEASURING AN IMPEDANCE RELATED TO TISSUE DEFINING A BOTTOM OF  │
│                       THE PILOT HOLE 536                        │
└─────────────────────────────────────────────────────────────────┘
```

FIG. 5

ROBOTIC SURGERY

CROSS-REFERENCE TO RELATED APPLICATIONS

This application claims benefit of priority from U.S. provisional application 63/124,627, which was titled "LASER SURGERY" and filed Dec. 11, 2020. The contents of this priority application is hereby incorporated herein by reference in its entirety for any and all purposes.

BACKGROUND

A wide variety of medical assemblies and systems have been developed. Some of these assemblies and systems include instruments used in surgeries. These assemblies and systems are manufactured by any one of a variety of different manufacturing methods and may be used according to any one of a variety of methods. Of the known medical assemblies, systems, and methods, each has certain advantages and disadvantages.

Among the medical assemblies and systems include laser assemblies and systems used to modify tissue. For example, carbon dioxide (CO2) lasers are used in skin-resurfacing. When applied to bone, because CO2 lasers hit a wavelength where bone has a higher absorption rate than water, the bone is superheated and vaporized. Holmium:Yttrium-Aluminum-Garnet (Ho:YAG) lasers are used to remove kidney stones. Since the absorption of Ho:YAG energy by the kidney stones relative to water is low, relatively high amounts of energy is needed to treat kidney stones. Erbium-doped:Yttrium-Aluminum-Garnet (Er:YAG) lasers have been used in bone removal in the jaw area. Saline has been used to cool a bone removal area.

SUMMARY

In a first example, there is a first example method for performing spinal surgery. The first method can include: exposing a vertebra of a patient; disposing a distal end of a laser instrument proximate the vertebra; conducting a laser-based topographical analysis of the vertebra using the laser instrument; registering a patient's anatomy using the laser-based topographical analysis; and creating a pilot hole in the vertebra with the laser instrument. The first example can further include: determining that the patient's spine shifted since a prior non-laser-based registration. The registering of the patient's anatomy can include updating an existing non-laser-based registration using the laser-based topographical analysis. Creating a pilot hole in the vertebra with the laser instrument can include creating a multi-diameter pilot hole. Creating the multi-diameter pilot hole can include creating a multiple diameter pilot hole having a countersink diameter and a minor dimeter interference. The first method can further include: placing a navigated instrument or an implant engaged with the navigated instrument into the pilot hole. The first method can further include: conducting a spectral analysis of laser reflection received through the laser instrument to determine laser characteristics to be used to complete a surgical plan. The first method can further include: registering a patient's anatomy using a non-laser registration technique to produce a non-laser registration; conducting a laser-based topographical analysis of the vertebra; and calculating a registration confidence value for the registration using the laser-based topographical analysis.

In a second example, there is a second example method including: removing a portion of facet joint tissue of a vertebra using laser energy transmitted from a distal end of a laser instrument, wherein the removing includes starting a laser cut on an outside of the facet and angling the transmission of the laser energy back into bone. The laser instrument can include an elongate shaft that defines a longitudinal axis. The laser instrument can define a laser pulse axis along which the laser instrument is configured to direct laser pulses. The laser pulse axis can be non-parallel with respect to the longitudinal axis. The second example can further include using a tissue dilator to expose spine tissue. The second example method can further include using laser topography, laser reflection, laser refraction, time of flight measurements, or optical coherence tomography to confirm when a cut is complete. Starting the laser cut on an outside of the facet and angling the transmission of laser energy back into bone can include using a mirror or angled laser fiber to perform the angling. Starting the laser cut on an outside of the facet and angling the transmission of laser energy back into bone can include angling the transmission of laser energy in a direction other than toward a disc or nerve. The second example method can further include extending the laser cut to undermine a spinous process proximate the facet joint and continuing the laser cut along a contralateral foraminal recess. The second example method can further include checking for range of motion limits that may dictate a patient re-orientation or a different tip with more angulation. The second example method can further include tuning a laser generator of the laser instrument such that generated laser pulses reach a frequency selected to cut a particular kind of tissue. The second example method can further include tracking the removing through laser topography, reflected laser energy, refracted laser energy, or optical coherence tomography to determine removed areas.

An third example method can include: exposing a vertebra of a patient; disposing a distal portion of a laser instrument proximate the vertebra; and creating a pilot hole in the vertebra, wherein the creating of the pilot hole includes repeatedly changing a direction of laser pulses emitted from the laser instrument. Changing the direction of the laser pulses emitted from the laser instrument can include: changing an angle at which laser pulses leave the laser instrument by changing an angle of a light director of the laser instrument; or changing an angle of a longitudinal axis of the laser instrument from a first angle to a second angle. Creating the pilot hole can include advancing the laser instrument toward the vertebra after removing a first amount of tissue from the vertebra and before removing a second amount of tissue from the vertebra. The third example method can include after creating the pilot hole, measuring an impedance related to tissue defining a bottom of the pilot hole to determine whether the tissue is bone.

A first example apparatus includes a laser instrument configured to selectively emit: a first laser pulses at a wavelength selected to affect disc tissue or cartilage tissue without ablating bone and a second laser pulses configured to interrogate a target region. The first example apparatus can further include a light detector configured to detect the second laser pulses; an irrigator configured to provide a fluid proximate tissue affected by the laser instrument to provide cooling and a medium to evacuate debris; and a suction generator configured to remove the fluid. The first example apparatus can further include a computer coupled to the light detector and having one or more processors configured to perform topographical analysis or spectral analysis based on the detected second laser pulses. The first apparatus can further include a laser generator configured to generate the first laser pulses according to parameters. The computer can be further configured to modify the parameters based on the topographical analysis or spectral analysis. The first example apparatus can include a reference array coupled to the laser instrument and configured to permit the tracking of a location of the laser instrument. The reference array can include two or more tracking fiducials. The first example apparatus can include a coupling configured to couple the laser instrument to a robot.

A fourth example method can include: receiving a selection of a tissue type over a user interface; providing an interrogation laser pulse to tissue; receiving the interrogation laser pulse from the tissue; determining an interrogated tissue type based on the received interrogation laser pulse; and providing a removal laser pulse to the tissue responsive to the interrogated tissue type matching the selected tissue type. The fourth example method can further include: determining an interrogated tissue thickness based on the received interrogation laser pulse; setting one or more parameters based on the determined interrogated tissue thickness; and generating the removal laser pulse according to the one or more parameters. The tissue type can be ligament tissue, disc tissue, tumor tissue, or bone tissue.

A fifth example method can include: disposing a distal portion of a laser instrument proximate a target region of bone of a patient where a pilot hole is to be created; and forming a pilot hole in the target region, wherein the forming includes applying laser energy from the laser instrument to the target region. The fifth example method can further include applying the laser energy includes to apply the laser energy in a sub-ablative manner with respect to the bone. The fifth example method can further include planning a procedure. Planning the procedure can include: receiving an indication of the location of the target region; receiving one or more characteristics of a screw to be disposed in the pilot hole; determining a characteristic of the pilot hole based on the one or more characteristics of the screw; and receiving confirmation of the determined characteristic of the pilot hole. The target region can be a region of a vertebra. The fifth example method can further include removing tissue proximate the target region such that the screw driver can reach a starting point of the screw and a posterior cortex of a spinal vertebra. The fifth example method can further include: obtaining a screw defining a screw cannula and a screw distal end; obtaining a screw driver defining a driver cannula; placing the laser instrument through the driver cannula; and placing the laser instrument into the screw cannula such that the distal portion of the laser instrument is proximate the screw distal end. The fifth example method can further include inserting the screw driver through the guide of a robot arm; and with a robot arm, disposing the guide proximate the target region. The fifth example method can further include after forming the pilot hole in the target region, driving the screw into the pilot hole using the screw driver. The fifth example method can further include: while forming a pilot hole in the target region: moving a robot arm under a surgeon's control or automatically according to a plan. The forming of the pilot hole can include calculating a depth of the pilot hole using the laser instrument. The laser energy can be in a spectrum associated with Er:YAG. The fifth example method can further include applying cooling using a cooling lumen. The fifth example method can further comprises applying suction with a suction lumen. The fifth example method can further include tracking a location with a navigation lumen.

A sixth example method can include forming percutaneous path through tissue to a target region of a vertebra; inserting a laser instrument into the percutaneous path such that a distal end of the laser instrument is disposed proximate the target region; and forming a pilot hole at the target region. The forming can include applying laser energy from the laser instrument to tissue of the target region. The sixth example method can further include applying laser energy from the laser instrument to remove soft tissue proximate the target region. Forming the pilot hole at the target region can include: detecting a tissue type of tissue to which the laser energy is to be applied; and modifying a laser energy level based on the tissue type. The detecting of the tissue type can include performing optical coherence tomography. The detecting of the tissue type can include performing spectroscopy. Applying the laser energy can include applying the laser energy in a manner that is sub-ablative with respect to bone. The applying the laser energy can include applying the laser energy in a manner that results in vaporizing water. The sixth example method can further include after forming the pilot hole, driving a screw into the pilot hole. The sixth example method can further include performing a topographical scan of the target region; determine whether the topographical scan sufficiently matches an expected result; and responsive to the topographical scan fails to sufficiently match the expected result, determining an appropriate offset transformation.

A second example apparatus includes a screw comprising a screw cannula, a screw head, and a distal tip. The second example apparatus can further include a screw driver comprising a drive tip and a driver cannula, wherein the drive tip is engaged with the screw head. The second example apparatus can further include a laser instrument extending through the screw cannula and the driver cannula, the laser instrument having a distal end disposed proximate the distal tip of the screw. The laser instrument can further include an adapter configured to optically couple a first laser conduit comprising silica glass to a second laser conduit and shift a wavelength of light entering the adapter from the first laser conduit from a wavelength of less than 2700 nanometers to a wavelength of greater than 2900 nanometers.

A seventh example method can include: determining a desired spinal implant geometry for a patient; obtaining an implant blank; intraoperatively shaping the implant blank with a laser; and implanting the shaped implant in the patient. The implant blank can be bone of the patient. Obtaining the implant blank can include cutting the implant blank from patient with the laser. The seventh example method can further include creating a pilot hole in a vertebra of the patient with the laser. Intraoperatively shaping the implant blank with the laser can include applying laser energy is in a spectrum associated with Er:YAG from the laser to the implant blank. Implanting the shaped implant in the patient can include implanting the shaped implant in an intervertebral space of the patient.

An eighth example method includes: obtaining a screw defining a screw cannula and a screw distal end; obtaining a screw driver defining a driver cannula; placing a distal end of an ultrasonic cutting probe through the driver cannula; placing the distal end of the ultrasonic cutting probe into the screw cannula such that the distal portion of the ultrasonic cutting probe is proximate the screw distal end; disposing the distal portion of an ultrasonic cutting probe proximate a target region of bone of a patient where a pilot hole is to be created; and forming a pilot hole in the target region, wherein the forming includes applying ultrasonic cutting energy from the ultrasonic cutting probe to the target region while the ultrasonic cutting probe extends through the screw cannula. The target region can be a region of a vertebra. The eighth example method can further include can further include removing tissue proximate the target region such that the screw driver can reach a starting point of the screw and a posterior cortex of a spinal vertebra. The eighth example method can further include: inserting the screw driver through the guide of a robot arm; and, with a robot arm, disposing the guide proximate the target region. The eighth example method can further include, after forming the pilot hole in the target region, driving the screw into the pilot hole using the screw driver. Forming a pilot hole in the target region can include moving the robot arm under a surgeon's control or automatically according to a plan.

A ninth example method includes forming a path through tissue to a target region of a bone; disposing a cutting apparatus proximate the target region; and a window in the bone with the cutting apparatus; removing a boney plug from the window; performing a procedure through the window; and replacing the boney plug in the window. The cutting apparatus can be a laser instrument. Cutting the window can include applying laser energy to the bone. The laser energy can be in a spectrum associated with Er:YAG. Applying laser energy to the bone can be sub-ablative with respect to bone. Applying the laser energy can include applying the laser energy in a manner that results in vaporizing water. The cutting apparatus can be an ultrasonic cutting probe. Performing a procedure through the window can include decompressing tissue through the window. The path can be an anterior path. The bone can be a vertebral body of a vertebra. The path can be a lateral path. The bone can be an iliac crest.

BRIEF DESCRIPTION OF THE DRAWINGS

FIG. 5 illustrates a third example method for creating a pilot hole in a vertebra.

DETAILED DESCRIPTION

Figure 1:
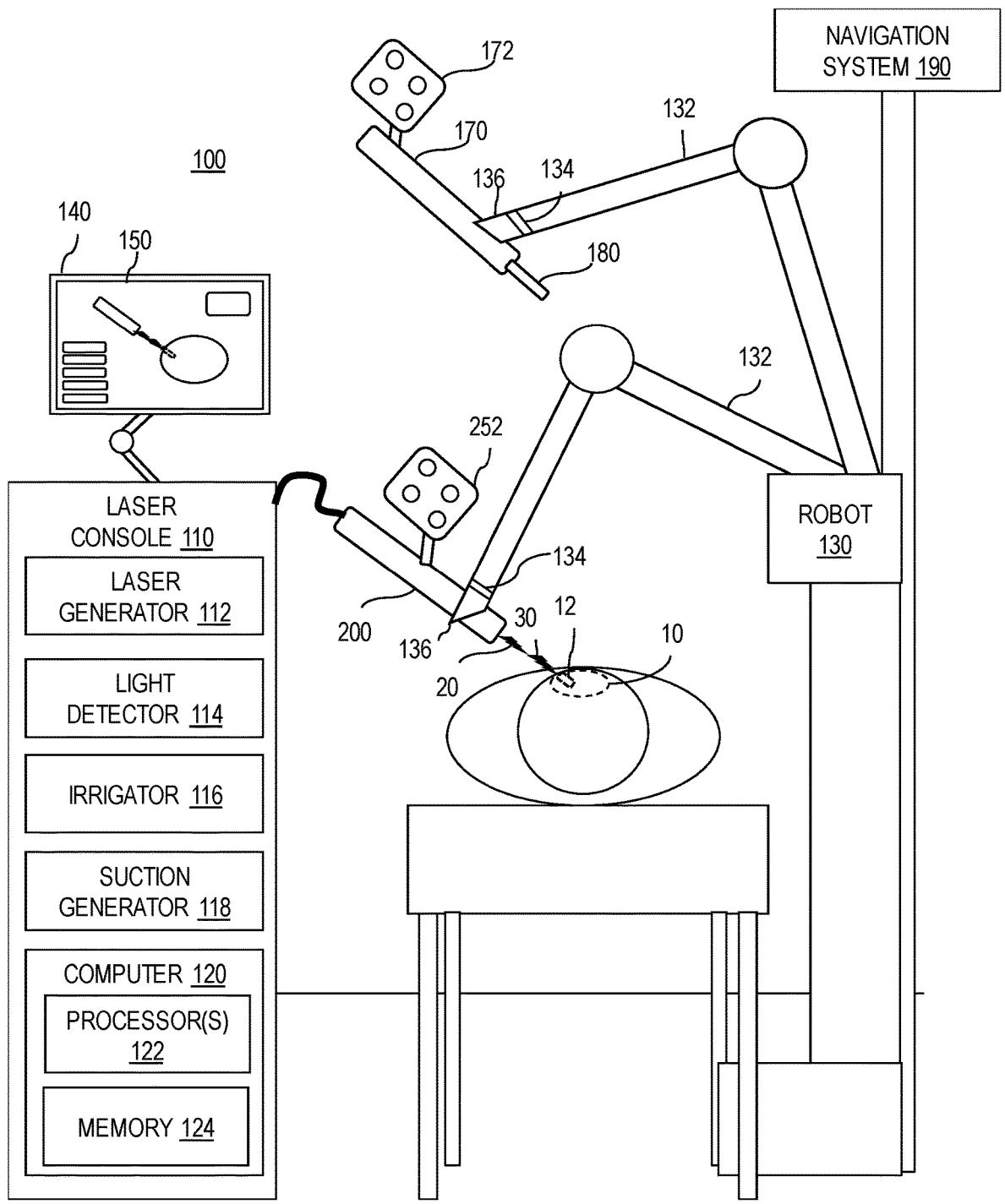
FIG. 1 illustrates an example laser surgery system.

Disclosed examples relate to the use of robot controlled cutting apparatuses in surgery. Examples include robot controlled lasers and robot controlled ultrasonic cutting apparatuses. The cutting apparatuses can be used for various aspects of surgery, such as for removing or shaping tissue. Lasers can be used for not only modifying tissue, but also navigation and tissue identification. While many examples herein are described in the context of spinal surgery, the devices and techniques herein can be applied to other kinds of surgeries. Laser and ultrasonic technologies have been applied to remove bone, but there are challenges in doing so. Aspects that affect the ability of a laser to remove bone include how well the wavelength of the laser is absorbed by water and how well the laser can modulate its power to vaporize water (e.g., instead of vaporizing bone).

Example techniques described herein can relate to surgical imaging, registration, navigation, and robotics. Example techniques for registration and intraoperative navigation is described in U.S. Pat. No. 9,510,771, filed Oct. 29, 2012, which is hereby incorporated herein by reference in its entirety for any and all purposes. Further examples of navigation, planning, and robotics are described in WO 2020/231880, which was filed in May 9, 2020, and WO 2021/062001, which was filed Sep. 24, 2020, both of which are hereby incorporated herein by reference in their entirety for any and all purposes. An example navigation system that implements surgical imaging, registration, and navigation is PULSE by NUVASIVE, INC., which includes navigation hardware and software. Example optical tracking hardware usable for some aspects of surgical navigation include the POLARIS VEGA by NORTHERN DIGITAL INC., and example optical tracking software includes application programming interfaces provided by the same. Example imaging devices include mobile C-arm imaging systems provided by SIEMENS HEALTHINEERS, PHILIPS, GE, MEDTRONIC, or others.

In an example, there is a method for using lasers to form a pedicle screw pilot hole. A system receives a pre-operative or intraoperative CT scan. The system receives implant planning input from a user, such as input specifying where one or more screws or expandable cages are to be placed. Intraoperatively, a surgeon places a hip pin or other implant for navigation. Intraoperative imaging is performed and the system registers the intraoperative image (that includes the hip pin) with the CT scan. A user adjusts or confirms the pre-op plan. A user places a surgical robot in an appropriate position, and the robot places a guide over a first pedicle location in the plan. An assembly that includes a screw, driver, and laser is locked in position proximate a starting point of the first pedicle. A surgeon hand guides the robot through programed movements with clutch to create pilot hole using the laser. The lock is released and the screw is placed in the pilot hole. For each remaining screw location, pilot hole creation and screw placement is repeated. A 3D scan is conducted to confirm appropriate placement of the screws.

In an example, there is a method for using a laser to remove tissue during a TLIF (transforaminal lumber interbody fusion) procedure. A pre-operative CT scan is performed. A user performs screw and expandable cage planning. Intraoperatively, a surgeon places a hip pin for navigation. Intraoperative imaging is performed and then registered with the pre-operative CT scan. A user adjusts or confirms the pre-op plan. A user places a surgical robot in an appropriate position, and the robot places a guide over a first facet location. A navigated dilator is placed over the facet per the plan by hand. Additional dilators are used to create an approximately 18 millimeter tubular retractor and locked in with articulating arm. This is tracked for simplified re-direction of contralateral decompression. The user uses a laser to trace the proposed removal path. The surgeon holds down a clutch and laser removes the desired bone and easy removal feature. The surgeon uses a rongeur or other instrument to remove the freed facet joint. Disc removal is performed. Endplate preparation confirmed with laser and navigation. A biologic and TLIF implant are packed in the appropriate location.

In an example, there is a method for open spine surgery with a laser. The method uses a laser to register the spine from a laser scan, create pilot holes from a plan using a laser, then use a laser to dynamically track the segmental movement of the spine during navigated instrumentation insertion into the pilot hole. The lasers used for these different operations can be the same or different lasers. A preoperative scan of the patient is performed and a preoperative plan for screws is constructed. The surgical team exposes the patient's operative site. A laser instrument is advanced to the operative site, and the laser is used to register the patient's anatomy through laser-based topographical analysis of the exposed anatomy. The method can be performed percutaneously.

Optionally, if the surgical team wants to use a pre-existing navigation registration method with a patient tracker, topographical registration can be used to determine whether the spine moved since the scan. If movement of the spine is detected, then the topographical segmental registration process can be performed to update the navigation and coordinate system.

Some implementations of the example include the use of a robot. The method can include using laser-based techniques to confirm that registration was correct (e.g. based on identifying locations of a starting hole, top of facet, top of spinous process, edge of lamina, or other locations). The locations identified using the laser-based techniques need not be the same points that a robot or surgeon used for topographical registration.

The laser is used to create a pilot hole for the implant or access an anatomic region. For example, a multiple diameter pilot hole with specific countersink and minor dimeter interference can be created to optimize pull out force and reduce insertion force for a multi-diameter screw.

Topographical and spectral analysis of laser reflection and refraction can be used to determine the relative depth to plan, tissue type, and relative energy to be applied to complete the plan while reducing the risk of damaging tissues beyond the planned area.

The laser is used to track the individual vertebral body segment topography, and adjusting the laser to keep real-time orientation relative to the vertebral body so a screw driver is synchronized with relative motion. A guide can be attached to the laser end effector (e.g., not in line with the laser) to place the navigated instrument, implant, or access into the prepared hole. The laser can be used to track the individual vertebral body segment topography, and updating the navigation relative tracking location of the movement from the vertebral body so that the display is updated in real time.

The navigated instrument can be controlled by a surgeon free hand to place the navigated instrument/implant/access into the prepared hole. Alternatively, a non-navigated instrument can be controlled freehand due to the optimized pilot hole's natural ability to guide the screw, although the screw's tip can be adapted to more ideally follow the pilot hole.

In an implementation, a laser pulse is transmitted through a fiber optic cable inserted through a cannulated screw to create a pilot hole then place the screw (e.g., a surgeon or robot can perform advancement). If the robot places the screw, an impedance mode can be used to permit the screw to follow the natural course of the pilot hole even with slight relative motion of the patient's spine. The fiber optic cable can be used to detect the reflection or refraction at the tip of the screw to detect tissue type and residual depth to plan with optical coherence tomography. This can be done through a guide tube releasably held by a robot so that as a surgeon decides to transition from pilot hole to screw insertion, the surgeon can gain relative axial motion on the guide.

In an implementation, the laser and the cannulated screw are collinearly arranged and then used to create the pilot hole and place the screw. For example, a surgeon places the screw via a guide attached to an end effector that has movement relative to the laser to make the two elements non-collinear so that the surgeon can drive the screw into the patient.

In another example, there is a method for using laser in an interbody fusion technique (e.g., transforaminal, lateral, posterior, or anterior interbody fusion of the cervical, thoracic, or lumbar spine) for gaining access, disc removal, fixation and lateral decompression.

The laser be embodied in, for example, a hand-held fiber-optic instrument or robot-based fiber-optic instrument. The laser can be in the form of a direct line of sight instrument or a non-direct line of sight instrument (e.g., a mirrored line of sight instrument).

The spine is registered for navigation using traditional techniques or via laser-based registration (e.g., as described elsewhere herein). A user identifies an amount of facet tissue to be removed in the scan and creates a plan for: facet removal, contralateral decompression, disc removal, pilot hole creation, other techniques, or combinations thereof.

In the example, during facet removal, a tissue dilator is used to protect the laser source from surrounding tissues and cut through the bone to be removed using topography, reflection/refraction and optical coherence tomography to confirm when the cut is complete and to resist cutting non-bone based tissues. Where the example includes a mini-open surgical technique, a tissue dilator need not be used. Using a mirror or angled laser, the cut can be started on the outside of the facet and angled back into bone rather than axially towards the disc/nerve. A robot can be used to track the progress and hold the laser precisely to improve safety and reduce heat buildup and accidental tissue contact.

During contralateral decompression, the same laser that performed the angled facet removal can also be used to extend that cut to undermine the spinous process and continue along the contralateral foraminal recess to make sure the nerve is not compressed. Using the re-registration process described elsewhere herein, a surgeon can maintain the plan even if screws or an interbody have been placed without needing to re-scan the patient with intraoperative imaging (e.g., fluoroscopy). The bone removal plan can be one continuous plan that allows the robot to check for range of motion limits that may dictate a patient re-orientation or a different tip with more angulation.

Laser energy can be tuned to hit specific frequencies that will be able to cut disc but not bone or vice versa. By placing the same angled instrument in the disc space the surgeon can create a plan on where the surgeon would like to have the laser hit for disc removal and track the progress through topographical, reflection/refraction, and optical coherence tomography to ensure that the target areas have been removed while reducing the risk of affecting adjacent tissues (e.g., as nerves or vessels) or damaging the endplates. This volume can then be relayed back to the user to create additional plans or to validate that the current plan is progressing as desired.

The laser instrument can be rotated or pivoted repeatedly to create a pilot hole. With each pass the laser instrument can be further inserted into the pilot hole until the desired depth has been removed. Additionally, topographical, reflection/refraction, or optical coherence tomography can be used to improve the likelihood that only planned tissue (e.g., bone) is removed. A robot can perform a final tap and measure the impedance at the end to confirm there is still bone at the end of the pilot hole.

In another example, there is a technique for using a laser to remove disc tissue, detect an amount of tissue removed, and avoid damaging endplates. For instance, using reflection, refraction, or optical coherence tomography a surgeon can more safely remove disc, even from the contralateral side of a transforaminal lumbar interbody fusion as well as decorticate while reducing a risk of breaking out of the disc space or damaging the endplates without removing the tool from the disc.

An example implementation can relate to addressing one or more clinical issues in TLIF procedures. For example, the laser instrument uses a spectrum of light specific to disc and cartilage that resists ablating bone. An irrigator creates a fluid environment near the laser to reduce the heat affected zone as well as provide a medium to evacuate micro-disc debris. A suction element evacuates the liquid along with any debris that is mixed into the medium that was not evaporated by the laser. A light detection element is used to detect reflected or refracted light for use in optical coherence tomography or other analysis techniques by a computer. An optional laser based tracking unit for the tip location even if there is deflection, although an infrared based navigation system can be used to track the handle instead, or no tracking at all (e.g., fluoroscopy is used to localize the tip).

Navigation and registration is performed using techniques described elsewhere herein. The surgeon optionally creates a plan for the amount of laser material the surgeon wants to remove, and the endplate that the surgeon wants to decorticate. Laser or other tracking can be used to determine where the tip of the laser instrument is inside the disc space. The tracking can be performed using a redundant system of infrared and laser to calibrate the laser system, and then let the changes in the system be updated by the laser system once the laser system is proximate the operative area (e.g., proximate the disc space). Deflection of the tip as the laser instrument is manipulated inside the disc space can affect accuracy of infrared-based navigation. The laser can then be activated when the laser instrument is inside an area preselected for removal. Reflection, refraction, or optical coherence tomography can be used to confirm that the laser instrument is cutting the desired disc material inside the selected zone. When the desired amount of tissue is nearly or completely removed, the system can inform the surgeon of the procedure's status so that the surgeon can more effectively place the instrument to remove other areas they had planned on treating. As the laser can be directed by mirrors or fibers, the instrument can have either a predefined angle or an adjustable angle to control and direct the laser pulses to particular locations. A robot can be integrated with this tool to provide an increase in precision, control and feedback loop to minimize the time to complete the disc removal. If no zone was planned, and no navigation used, then the reflection, refraction and optical coherence tomography can be used to reduce the likelihood of the surgeon accidentally removing non-disc tissue (e.g., ligament, nerve, vessel, or endplate tissue). During laser activation irrigation flows through a distal lumen in the direction of the light pulses (e.g., aligned with mirror or fiber mechanism). A second lumen provides suction to evacuate the micro-debris that is evaporated when the laser pulse is fired.

In another example, there is a technique for using a laser to identify and then selectively remove high risk tissues (e.g., tumor, trauma debris, transforaminal lumbar interbody fusion tissue, and anterior column realignment tissue). A computer receives, from the surgeon, input regarding the type of tissue that the surgeon wants to remove (e.g. ligament, disc, or tumor). The computer can integrate with a navigation and robotics system to gain an additional level of localization and precision of control over the tip of the laser instrument. Fluoroscopy can be used for localization. The computer can receive a plan for the specific affected area on a 3D scan or a merged scan (e.g., the merger of two different 3D scan types, such as MRI or CT) to gain better localization of the high risk tissue through segmentation. A laser instrument is inserted proximate the area and before each set of laser pulses, the computer identifies the tissue to be removed, its relative thickness and then alters the laser's power setting to increase the likelihood of removing only the selected tissue type. The computer can receive surgeon preference regarding whether to remove with a margin, up to the boundary, or with an additional over border beyond the targeted type and area. The device need not require navigation and planning as the tissue discrimination integration can facilitate removal of only the desired type of tissue. Laser navigation can be beneficial when 3D orientation or specific locations are important and cannot be directly visualized.

In an example, Er:YAG lasers are used to remove bone. Er:YAG lasers operate at a wavelength of approximately 2940 nanometers. Beneficially, this wavelength corresponds to an approximate wavelength region where water absorbs laser energy at approximately two orders of magnitude higher levels than bone (hydroxyapatite). This difference means that when the laser light of that wavelength affects an area of bone and water, the water in the area flashes into steam and explodes (e.g., forming an explosion of less than approximately one millimeter cubed) and disintegrates the surrounding bone. However, the bone does not absorb significant heat from the laser, and the flash vaporization functions as primarily mechanical destruction. Application of such laser energy tends to not produce a char. The wavelength of Er:YAG lasers is such that, when used to remove bone, the laser energy heats water sufficiently quickly that the resulting expansion explodes the affected fragments away from the original bone. This explosion leaves a cancellous structure behind that allows blood to flow through and promote healing and fusion if needed. The wavelength of Er:YAG lasers is, however, beyond a typical silica optical fiber transmission range, and so sapphire-based glass is often used to transmit the Er:YAG light. In order to reduce cost, a segment of the laser energy can be generated with a diode pump and silica fiber (e.g., glass fiber), then the last approximately twenty to thirty centimeters of fiber can by interrupted and a Er:YAG adapter is placed to couple the silica glass to the sapphire glass fiber. This adapter arrangement can keep the generator more cost effective, the initial part of the cable more cost effective, but still results in a spectrum of light that is in the Er:YAG zone that correlates with the peak in the water absorption curve. Additionally, the Er:YAG adapter can have additional parallel functions that will be used for depth and tissue discrimination based on spectroscopy.

In an example technique, an Er:YAG laser is used to create a percutaneous pedicle pilot hole. A laser fiber is attached to a cannulated screw and screw driver such that the laser fiber is close to the distal tip of the screw. The laser fiber is used to transmit energy of the Er:YAG spectrum into the spinal anatomy that is targeted for pilot hole creation. The laser fiber or another set of fibers can have secondary functions to receive reflect light for use in determining a depth of penetration (e.g., based time of flight principles). The laser fiber or another set of fibers have a further function in use of spectroscopy to compare the wavelengths reflected to a look up table of known tissue light parameters and identify important tissues types (e.g., cortical, cancellous, nerve, and disc), which can be used to control the laser energy. Laser pulses for energizing water vapor to excavate bone can be interwoven with the sensing of depth and tissue type. In some examples, one or more cooling lumens are inserted into the screw driver for use in providing cooling. In some examples, one or more suction lumens extend through the to remove debris from the bone removal site. In some examples, a fiber optic navigation lumen is present to track the location of the tip of the screw.

The example technique can take the form of a robot assisted single step screw insertion. The surgeon plans screw placement on a 3D scan of the patient. One or more intraoperative or preoperative CT scans are used for navigation. Once the screws are chosen, correlated pilot hole diameters are automatically recommended and may be edited by a surgeon. The surgeon reviews and confirms the screw insertion plan. The robot loads its base location and determines that it has sufficient range of motion to follow the screw insertion plan. The robot places a tubular guide over the spine where the first screw was planned. The surgeon uses a scalpel to cut the skin and fascia so that the screw driver can reach the starting point of the screw and the posterior cortex of the spinal vertebral body. The laser fiber is placed through the cannulation of the screw and screw driver to a location proximate the distal portion of the screw and locked into place. The screw driver and fiber assembly is then placed through the robot screw guide and rigidly locked into place. A pilot hole cutting program is then executed automatically to create the desired pilot hole in the spine at the planned position. In one implementation, the cutting is performed in cooperation with a surgeon using collaborative hand guiding that is restricted to only allow movements of the arm by the surgeon within the planned pilot hole area. In another implementation, the robot leads the surgeon through the cutting plan with the surgeon acting as observer ready to intervene if the surgeon determines that the robot should stop cutting. In addition, or instead, the surgeon can lead the robot through the volume to be cut. A user interface can show the areas of tissue that have been affected and display an alert if a monitoring system (e.g., a monitoring system using laser pulses to determine depth of cutting and tissue type) determines that there is an error in depth, an error in tissue type, or when the pilot hole is completed. Once the pilot hole is completed, the surgeon disengages the robot guided tube lock and place the screw using the driver. The laser can remain inside the screw driver if needed to continually check the tissue type, or even continue to cut so that the screw does not have to remove all of the bone by itself.

Where fiber optic navigation is used, the monitoring system can provide an alert if there is a significant deviation from the plan. In some examples, between each level of bone removal, the laser fiber (or another fiber) is used to perform a topographical scan of the pilot hole area for use in confirming that the area matches a segmentation from a scan. If there is not a match, then the system can perform a cross correlation to determine what offset transformation matrices need to be adjusted to align with the appropriate topographical section on the vertebral body. Such a process can obviate the need to rescan or redo 3D/2D registration. In an example, where multiple spinal levels are exposed, a C-arm can be replaced with the laser topographical references and no intra-operative registration, or fiducials for tracking are needed. If an incorrect tissue type is detected or if there is another kind of error, then the surgeon can replace the laser fiber with a Kirschner wire and then perform 2D intraoperative imaging to help the surgeon visualize on 2D imaging regarding how far and where the laser has cut by visualizing the location of the wire.

Certain implementations are configured to be efficient with each pulse into the tissue. A laser pulse removes an amount of tissue with each light pulse, and the laser instrument can be configured to avoid building up heat and destroying the living bone cells. For example, a robot can be used to achieve these aspects by moving the laser instrument in a pre-planned pathway and to a controlled depth.

Bone cutting or pilot hole cutting software application can be incorporated as a part of screw or surgery planning software. Interactive software can be provided that receives, from a user, the area at which tissue is to be cut (e.g., a facet for transforaminal lumbar interbody fusion).

Depth can be detected based on laser pulses or based on detected tissue types. Distance to a solid object can be detected a laser and a detector using, for example, time of flight determination. Tissue detection can be performed based on optical coherence tomography or a combination of spectroscopy and 3D navigation to anticipate the bone type change and correlate the bone type change back to location on a CT scan to confirm that the actual location and perceived location match. In an example, optical coherence tomography is used to detect imminent tissue changes (e.g., a transition from cancellous to cortical bone, or exiting the cortical bone altogether).

Tissue identification software can be beneficial when the patient shifts (e.g., as a result of implanting an implant in the patient or as a result of repositioning the patient). Spectroscopic techniques can be used to determine the difference between different categories of tissue (e.g., bone, tissue, nerve). Spectroscopic techniques can be relatively faster. More advanced categorization (e.g., determining which bone layer is being examined) can be performed using optical coherence tomography. The system can include a detector to perform such techniques. The results can be used to, for example, control energy of the laser pulses based on the tissue type being cut and can be used to stop removal if the detected tissue type is contraindicated for cutting (e.g., nerves). In some examples, the lumen and laser used for the interrogation laser (e.g., for depth and tissue type determination) are separate from the cutting laser and lumen. In other examples, interrogation and cutting laser pulses can be interleaved.

An irrigation pathway is used for cooling and to evacuate bone dust or other debris. A suction pathway can be used to evacuate blood, cooling fluid, bone dust, and other debris. A filter and analysis station (e.g., on a cart) can be used to evaluate potential for charring on the evacuated debris (e.g., bone dust) retrieved via suction or irrigation. Responsive to detecting charring in the debris, one or more parameters of the cutting can be changed (e.g., laser intensity or cutting plan location). A fiber optic based navigation system can be used to permit the surgeon to ascertain where the tip of the laser instrument is in case the actual position is too far deviated from the planned position.

In an example implementation, the laser instrument is attached to or otherwise held by a robot arm with the laser generator being rigidly attached to the robot arm so there is a straight shot through the internal diameter of the device or a hollow core light guide (e.g., wave guide) with gentle radii is used to link the laser instrument to a laser generator on a cart. In an example, the laser instrument or a guide tube has at least two diameter steps: a first diameter step for going into the bone and a second diameter step that is rigid and meant to prevent deflection from slight movement inside the tissue planes. In an example, the laser instrument includes one or more lumens configured to carry irrigation. In an example, the laser instrument includes one or more lumens via which fluid can be removed. In an example, the laser instrument includes one or more lumens configured to transmit detection optical coherence tomography laser light down. In an example, the laser instrument includes one or more lumens configured to receive (e.g., read) the optical coherence tomography reflection, or is it done in series through the same lumen). In an example, the laser instrument includes one or more lumens configured to perform laser/fiber optic based navigation of the tip. In an example, the laser instrument supports the optical coherence tomography laser. In some examples, the laser instrument includes multiple light guide fibers fused together. In an example, the size of the diameter of the tip of the instrument is less than the desired pilot hole size so that the distal portion of the instrument can enter the pilot hole as the pilot hole is being made and effectively detect tissue type, cool, and evacuate debris. In an example, the tip of the laser instrument has a diameter of approximately 3 mm. In another example, the tip is larger (e.g., approximately seven to eight millimeters) to allow for the evacuation of cut disc material. In an example, a mirror or another laser directing device is placed at the tip of the device to provide an off axis laser beam that is used in a rotational method in addition to stepping into the anatomy that it is cutting.

In an example method, a surgical robot travels to a planned position over the patient's skin. A surgeon would create a skin incision at the planned position. A tissue displacing cannulated rigid instrument can be used to blunt dissect through tissue (e.g., muscle) down to the anatomy that is to be removed. The can traverse the fat and muscles at the planned position to reach the planned cutting area (e.g., the desired location of the pilot hole). The robot applies optical coherence tomography or spectroscopy to determine tissue depth and tissue type. The laser generator adjusts its power according to tissue type and depth. The laser is activated to remove residual soft tissues layers on top of the bone. The laser detects the tissue type change (e.g., from soft tissue to bone) and adjusts a power profile to cut cortical outer layer of bone. Irrigation is applied to cool the area and suction is applied to evacuate fluids. During cutting, the depth of each cutting pulse or set of cutting pulses is analyzed and the power adjusted to improve cutting speed while reducing the risk of charring surrounding tissues. The optical coherence tomography or spectroscopy detects the transition from cortical to cancellous tissue and the laser parameters are further adjusted to improve cutting speed. The optical coherence tomography or spectroscopy detect any unexpected tissues and can stop or adjust the cutting (e.g., to avoid cutting such as nerves or providing an alert if encountering cortical bone earlier than expected). Depth is detected and stopped when the depth is aligned with the plan if no unexpected tissues were encountered. The laser instrument retracts and a navigated screw driver (e.g., navigated using fiber optics or infrared arrays) is then be placed in the hole. This process is repeated for as many screws as wanted.

The cutting pathway can be rotated through a diameter that is larger than the tip of the laser instrument if the aspect ratio of the planned cut exceeds the optical coherence tomography tissue detection range or the suction's ability to evacuate cooling fluid and blood. If the laser instrument is just being used to cut facet tissue, then the laser instrument can be stood off at the posterior cortex during use. If the laser is cutting a long pilot hole, then the laser instrument may need to enter the pilot hole to ensure that the cutting is going according to plan.

In an example method, a pilot hole is created at the same time as the screw is inserted. For example, the method is a single step method by shooting a beam through a cannulation of the screw. For instance, the laser can be fired through the air gap on a cannulated driver and screw. The creation of the pilot hole can begin with the screw/laser moving through a prescribed robot pathway standing off of the posterior cortex until the cortical bone is removed so that the initial screw threads can bite into the underlying layer of bone. Once the initial layer of bone is removed and the screw is started the driver will move it through the pedicle, so no laser is needed.

In an example open pilot hole method, the laser instrument emits the laser to cut the pilot hole directly onto the bone and spray saline in the affected area to keep surrounding tissues from reaching a char temperature.

In an example, the same or similar approach as described in creating a pilot hole with a robot can be done freehand to remove disc material with the tip tracked via the fiber optic navigation system. In an example, a suction lumen is stuck into or near the disc and cored material that gets in the way is be removed. Tip tracking is used to show where the cores have been removed and where the disc still remains. An additional tool that has a bevel tip to allow for angulation up, down, and rotationally around can be used to treat the cartilaginous endplate. In an example, due to the differences between bone and disc tissue, the laser type used to remove disc tissue is Neodymium-doped:Yttrium Aluminum Garnet (Nd:YAG). In an example, the disc tissue is ablated.

In still further examples, one or more of the above techniques or devices can be modified to use an ultrasonic cutting apparatus to cut bone or other tissue. For example, a robot can control an ultrasonic cutter to remove tissue, such as to form a pilot hole.

In yet another example, the laser or another cutting apparatus is used to form a window in a vertebral body for decompression. In a still further example, the laser or another cutting apparatus is used to from a window or notch in the patient's iliac crest to form a window through which a procedure can be performed.

The above techniques and devices can be implemented using a system. In an example, that system is the same as or is similar to the one described in FIG. 1.

Example Laser Surgery System

FIG. 1 illustrates an example laser surgery system 100. As illustrated, the system 100 includes a laser console 110, a robot 130, a display 140, an instrument 170, an implant 180, a navigation system 190, and a laser instrument 200.

In an example, the laser console 110 is a cart that carries one or more components used to provide laser functionality and other features. In the illustrated example, the laser console 110 includes a laser generator 112, a light detector 114, an irrigator 116, a suction generator 118, and a computer 120. In other examples, the laser console 110 includes one or more other components or one more of the components are provided elsewhere in the system 100 (e.g., the laser instrument 200 carries the laser generator 112 and the light detector 114).

The laser generator 112 is a component configured to generate laser pulses 20, 30. For example, the laser generator 112 can be configured to generate the first laser pulses 20 according to first parameters and generate the second laser pulses 30 according to second parameters. In an example, the laser generator 112 comprises a diode pump. In some examples, the laser generator 112 is configured to generate laser pulses 20, 30 in a wavelength spectrum associated with particular target tissue to be affected. For example, where the target tissue is bone, the laser generator 112 is configured to generate laser pulses 20, 30 at a wavelength selected to affect bone, such as a wavelength in a spectrum associated with Er:YAG. In some examples, the laser generator 112 is optically coupled to the laser instrument 200 such that laser pulses 20, 30 generated by the laser generator 112 are transmitted to and emitted by the laser instrument 200 at a desired target. In some examples, the wavelength of the laser pulses 20, 30 does not substantially change as the laser pulses 20, 30 are conducted between the laser generator 112 and the laser instrument 200. In other examples, the laser generator 112 generates laser pulses 20, 30 at a first wavelength and the wavelength is shifted to a second wavelength by the laser instrument 200. As a specific example, the first wavelength is a wavelength suitable for transmission via a silica optical fiber and the last approximately twenty to thirty centimeters of fiber (e.g., at the laser instrument 200) is interrupted by an Er:YAG adapter that shifts the wavelength of the light into a second wavelength (e.g., a wavelength associated with an Er:YAG spectrum) and transmits the shifted laser pulses 20, 30 into sapphire glass fiber for transmission to the distal portion of the laser instrument 200. In an example, the laser generator 112 is electrically coupled to the computer 120 such that the computer 120 can control the laser generator 112, such as by activating the laser generator 112, deactivating the laser generator 112, or modifying one or more parameters by which the laser generator 112 operates.

The light detector 114 is a component configured to detect light. For example, the light detector 114 can be configured to detect laser pulses 30 produced by the laser instrument 200 and reflected off tissue of interest. For instance, the light detector 114 is optically coupled to the laser instrument 200 (e.g., using a same or different optical fiber as the one used to provide laser pulses 20, 30 to the laser instrument 200 from the laser generator 112) such that light collected proximate the distal portion of the laser instrument 200 (e.g., laser pulses reflected off of tissue of the patient) is transmitted to and detected by the light detector 114. The light detector 114 can be electrically coupled to the computer 120 such that data regarding detected light (e.g., timing and wavelength) is communicated to the computer 120 for use in processing. In some examples, the light detector 114 includes temperature-sensing capability (e.g., using infrared temperature detection) configured to detect a temperature at an area of tissue being affected by the laser instrument 200. The sensed temperature can be used to modify treatment of the tissue (e.g., to activate cooling of the tissue or to modify an intensity of the laser pulses).

The irrigator 116 is a component configured to provide fluid (e.g., a liquid or gas) for use in irrigating a target area. For example, the irrigator 116 can be configured to provide a fluid proximate tissue affected by the laser instrument 200 to provide a medium to evacuate debris formed during the application of the laser pulses 20, 30. The fluid can serve alternative or multiple purposes, such as to provide cooling to the laser instrument 200 or cool target tissue. In many examples, the fluid is a sterile liquid (e.g., saline) stored in a reservoir. In other examples, the fluid is a gas. The irrigator 116 can be fluidly coupled with the laser instrument 200 or another instrument such that fluid provided by the irrigator 116 (e.g., moved by a pump of the irrigator 116) is expelled proximate the distal portion of the laser instrument 200 (e.g., proximate an area of tissue being affected by the laser instrument 200).

The suction generator 118 is a component configured to generate suction. For example, the suction can be configured to remove fluid, debris, or other material from proximate a target region. The suction generator 118 can be fluidly coupled with the laser instrument 200 or another instrument such that material proximate the distal portion of the laser instrument 200 (e.g., fluid provided by the irrigator 116 and debris) is evacuated from the area. In an example, the suction generator 118 includes or is coupled to a container for storing the material evacuated by the suction generator 118. In an example, the suction generator 118 includes one or more sensors configured to analyze evacuated materials (e.g., for charring or tissue type determination). The sensors or other components of the suction generator 118 can be communicatively coupled with the computer 120 for providing output or receiving input. In some examples, the suction generator 118 can be used to evacuate air from the area to reduce an odor caused by treating the tissue.

Figure 10:
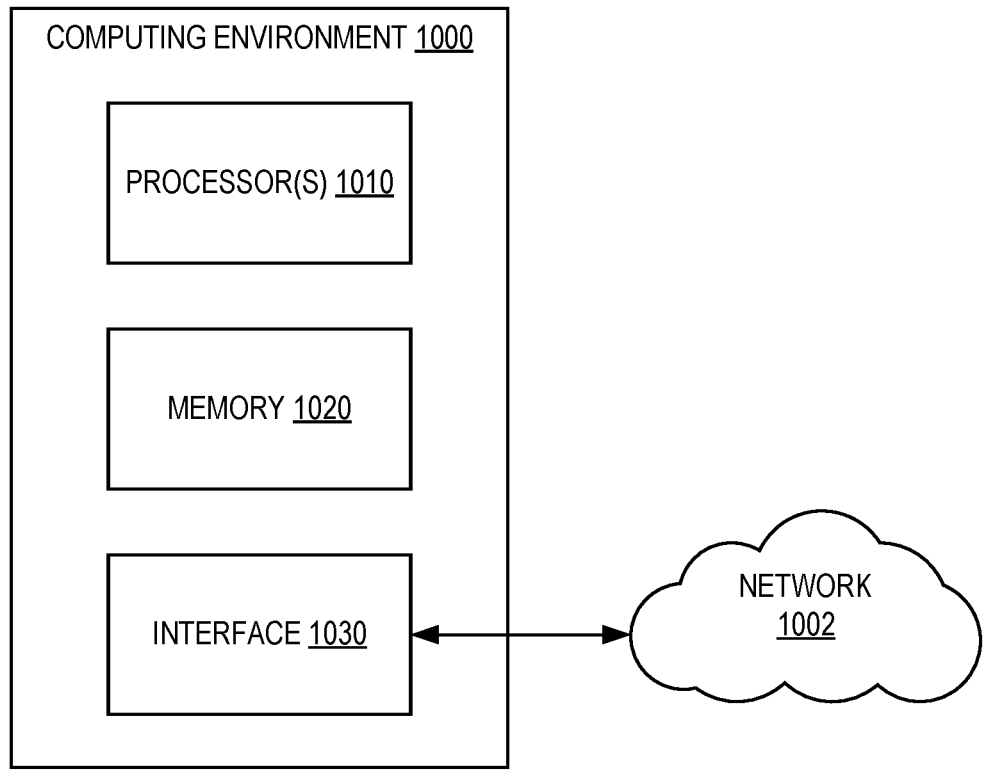
FIG. 10 illustrates an example computing environment with which techniques described herein can be implemented.

The computer 120 can be a computing environment, such as the one described in more detail in FIG. 10. In the illustrated example, the computer 120 includes one or more processors 122 and memory 124, which can correspond to the processors and memory described in relation to FIG. 10. In an example, the memory 124 stores one or more programs or instructions that, when executed by the one or more processors 122 cause the one or more processors 122 to perform one or more operations as described herein. In an example, the computer 120 is configured to control the laser generator 112, receive data from the light detector 114, control the irrigator 116, control the suction generator 118, provide data to the display 140, receive data from the display 140 (e.g., where the display is a touch screen), and receive data from one or more user interface elements (e.g., buttons or controllers). In an example, the computer 120 is coupled to the light detector 114, and the one or more processors 122 are configured to perform a topographical analysis or a spectral analysis based on laser pulses 30 detected by the light detector 114. The one or more processors 122 can change one or more parameters used by the laser generator 112 based on the results of the topographical or spectral analysis. In some examples, the computer 120 controls the robot 130. In some examples, the computer 120 receives commands from the robot 130. In some examples, the computer 120 controls the navigation system 190. In some examples, the computer 120 receives commands from the navigation system 190.

The robot 130 is a surgical robot. The robot 130 can include one or more arms 132. As illustrated, a first arm 132 has the laser instrument 200 as an end effector 136 and a second arm 132 has an instrument 170 with an implant 180 attached as its end effector 136. The one or more arms 132 each include a coupling 134. The coupling 134 is a component that couples a robot arm 132 to an end effector 136. In an example, the end effector 136 is a component configured to hold and control a tool, such as a guide for a tool. In an example, the end effector 136 is the tool itself.

The robot 130 can be configured to move its one or more arms 132 according to a movement plan. For example, the robot 130 can move the laser instrument 200 through a particular cutting plan. In an example, the robot 130 cooperates with the computer 120 to obtain (e.g., from a user or file) and execute the cutting plan. The robot 130 can be implemented in any of a variety of ways. In an example, the robot 130 is an LBR IIWA by KUKA ROBOTICS CORPORATION. Such a robot can be programmed, controlled, or operated using software such as IIQKA.OS or SUNRISE.OS by KUKA ROBOTICS CORPORATION. Further details that the robot 130 can be implemented with include those described in WO 2020/231880 and WO 2021/062001, which were both previously incorporated herein by reference.

The display 140 is a set of one or more visual output components (e.g., liquid crystal displays or organic light emitting diodes). In some examples, the display 140 includes or is coupled with a touch-sensitive input device (e.g., making the display 140 a touch screen). The display 140 can provide a user interface 150 in an example, the user interface 150 provides data to a user of the system 100 regarding the operation of one or more components of the system 100.

Figure 8:
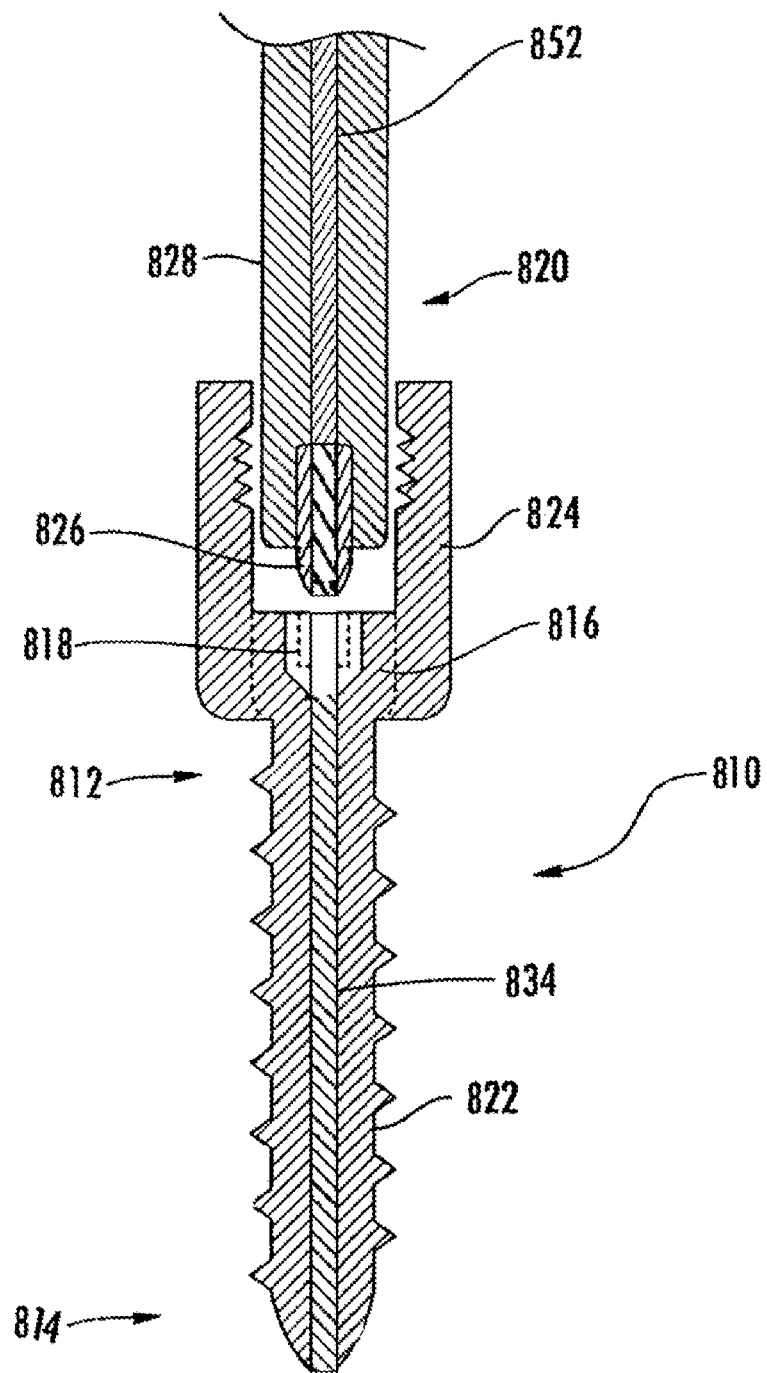
FIG. 8 illustrates an example apparatus including an example cannulated screw and driver with the laser instrument inserted through the cannula.

The instrument 170 can include a tool for use during surgery, such as a drill as described in more detail in relation to FIG. 8. The instrument 170 is coupled to a tracking array 172. The tracking array 172 can be a component that cooperates with the navigation system 190 to facilitate the determination of the location of the instrument in space. For example, the tracking array 172 can include one or more active or passive infrared fiducials configured to be detected by the navigation system 190.

The implant 180 is a component configured to be temporarily or indefinitely implanted in the patient. An example implant 180 is a screw, such as the screw described in relation to FIG. 8.

The navigation system 190 can be a system of one or more components configured to provide a user the ability to leverage intraoperative imaging in real-time to provide spatial awareness between anatomical structures and instrumentation, such as in relation to pre-operative 3D scans of the patient. An example navigation system 190 includes one or more optical tracking components configured to detect (e.g., using visible light or infrared light) in real-time location of objects in relationship to each other as the objects move through space. Using the optical tracking system, the navigation system 190 can obtain usable to determine the location of one or more tracking arrays, which can be used to provide dynamic 3D position information corresponding to the anatomical features, the surgical instruments, and the surgical implants being tracked. An example navigation system 190 that can be used to implement one or more of the aspects described herein is PULSE by NUVASIVE, INC., which includes navigation hardware and software. Example optical tracking hardware include the POLARIS VEGA by NORTHERN DIGITAL INC., and example optical tracking software includes application programming interfaces provided by the same.

The laser instrument 200 is an instrument configured to selectively emit laser pulses 20, 30. The illustrated laser instrument 200 is configured to selectively emit first laser pulses 20 configured to affect tissue and second laser pulses 30 configured to interrogate a target region. For example, the first laser pulses 20 can be at a wavelength selected to affect disc tissue or cartilage tissue without ablating bone. In some examples, the first laser pulses can be configured to ablate tissue. As illustrated, the laser instrument 200 is coupled to a reference array 252. The reference array 252 can be configured to permit the tracking of a location of the laser instrument 200 by the navigation system 190. In an example implementation, the reference array 252 includes two or more tracking fiducials 254. Additional details regarding the laser instrument 200 are shown and described in relation to FIG. 2.

Laser Instrument

Figure 2:
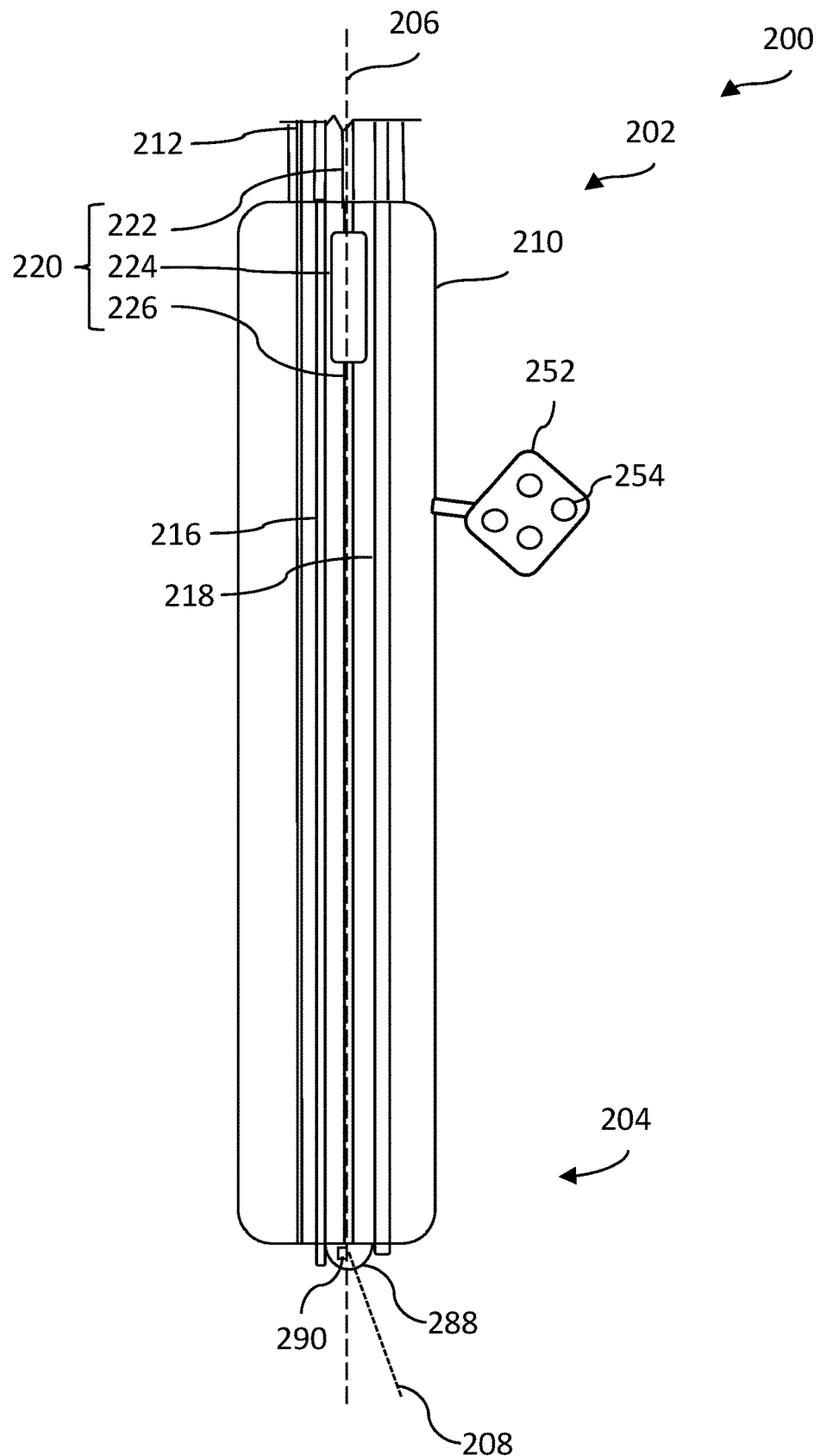
FIG. 2 illustrates an example laser instrument.

FIG. 2 illustrates an example implementation of the laser instrument 200. The laser instrument 200 defines a proximal end 202 and a distal end 204. The illustrated laser instrument 200 includes an elongate shaft 210 that defines a longitudinal axis 206. The laser instrument 200 further defines a laser pulse axis 208 along which the laser instrument 200 is configured to direct laser pulses 20, 30. In the illustrated example, the laser pulse axis 208 is non-parallel with respect to the longitudinal axis 206. In some examples, the laser pulse axis 208 and the longitudinal axis 206 are parallel. In some examples, the angle between the laser pulse axis 208 and the longitudinal axis 206 is manually or automatically configurable.

The illustrated laser instrument 200 includes a navigation lumen 212, a cooling lumen 216, a suction lumen 218, and a laser conduit 220. The laser instrument 200 is coupled to a reference array 252.

The navigation lumen 212 is a component of the laser instrument 200 configured to facilitate navigation of the laser instrument 200. In an example, the navigation lumen 212 is or includes a bundle of one or more optical fibers arranged to facilitate tracking. Example fiber optic tracking bundles include those described in U.S. patent application Ser. No. 17/474,537, which was filed Sep. 14, 2021, and which is hereby incorporated herein by reference in its entirety for any and all purposes. In another example, the navigation lumen 212 is configured to operate as an endoscopic camera to permit a user to visualize an area proximate the distal end 204 of the laser instrument 200 (e.g., at the display 140).

The cooling lumen 216 is a lumen configured to transport cooling or irrigation fluid to an area proximate the distal end 204 of the laser instrument 200. In an example, the cooling lumen 216 is in fluid communication with the irrigator 116 such that irrigation provided by the irrigator 116 is provided through the cooling lumen 216.

The suction lumen 218 is a lumen configured to carry away material proximate the distal opening of the suction lumen 218. In an example, the suction lumen 218 is in fluid connection with the suction generator 118. The suction generator 118 can induce suction through the suction lumen 218 to cause suction to remove material from proximate the distal end of the suction lumen 218.

The laser conduit 220 is a component configured to conduct laser pulses 20, 30 received by the laser instrument 200 (e.g., from the laser generator 112) to a desired location proximate the distal end 204 of the laser instrument 200. In the illustrated example, the laser conduit 220 includes a first laser conduit 222, a laser adapter 224, and a second laser conduit 226. The first laser conduit 222 is a portion of the laser conduit 220 having first properties. In an example, the first laser conduit 222 includes properties optimized in a first way (e.g., for cost, flexibility, or durability rather than wavelength compatibility). In an example, the first laser conduit 222 comprises silica glass. The laser adapter 224 is a component configured to optically couple the first laser conduit 222 to the second laser conduit 226. The laser adapter 224 can be configured to shift a wavelength of laser pulses 20, 30 entering the adapter 224 from the first laser conduit 222. For example, the adapter 224 can be configured to shift from a wavelength of less than 2700 nanometers to a wavelength of greater than 2900 nanometers. The second laser conduit 226 is a portion of the laser conduit 220 having second properties. In an example, the second laser conduit 226 includes properties optimized in a second way (e.g., for wavelength compatibility rather than cost, flexibility, or durability). In an example the second laser conduit 226 comprises sapphire.

The reference array 252 can be configured to permit the tracking of a location of the laser instrument 200 by a navigation system. In an example implementation, the reference array 252 includes two or more tracking fiducials 254. In an example, the tracking fiducials 254 are infrared retroreflectors. In another example, the tracking fiducials 254 are active infrared lights.

In some examples, the laser instrument 200 includes a laser tip 288. In an example, the laser tip 288 is a component configured to facilitate the laser pulses 20, 30 exiting the laser instrument 200. For example, the laser tip 288 can be configured to facilitate the transition from the material of the second laser conduit 226 (e.g., sapphire) to air. In an example, the laser tip 288 includes a lens.

In the illustrated example, the laser instrument 200 includes a light director 290. The light director 290 can include a mirror or lens configured to modify an angle of a laser pulse 20, 30 exiting the laser instrument 200. In some examples, the mirror or lens is configured to have its position modified (e.g., by the computer 120).

The components described in FIG. 1 and FIG. 2 can be used to perform any of a variety of methods, such as those described in relation to FIGS. 3-7 and 9.

First Example Method

Figure 3A:
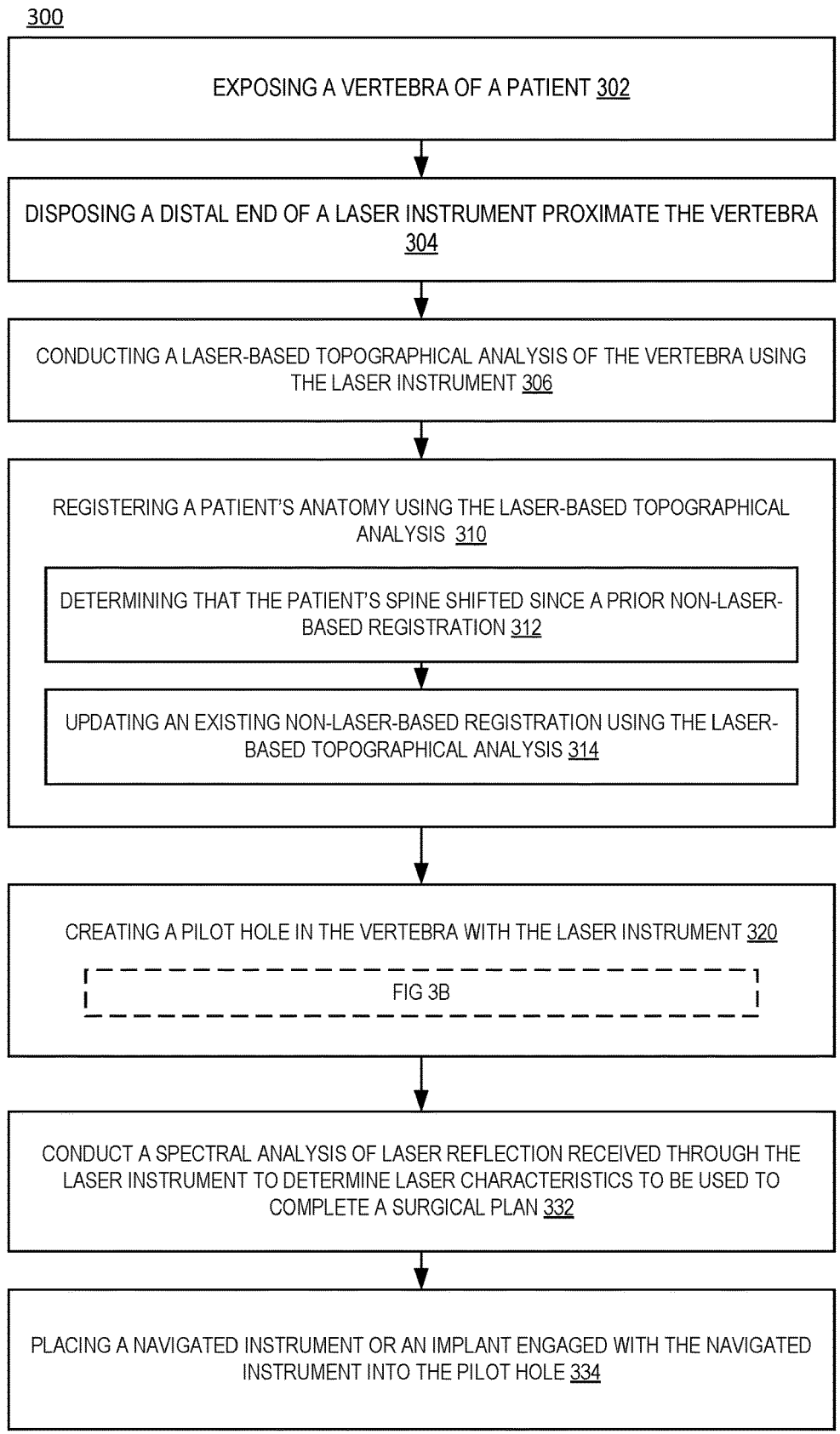
FIG. 3, which is made up of FIGS. 3A and 3B, illustrates an example method for performing spinal surgery using a laser.
Figure 3B:
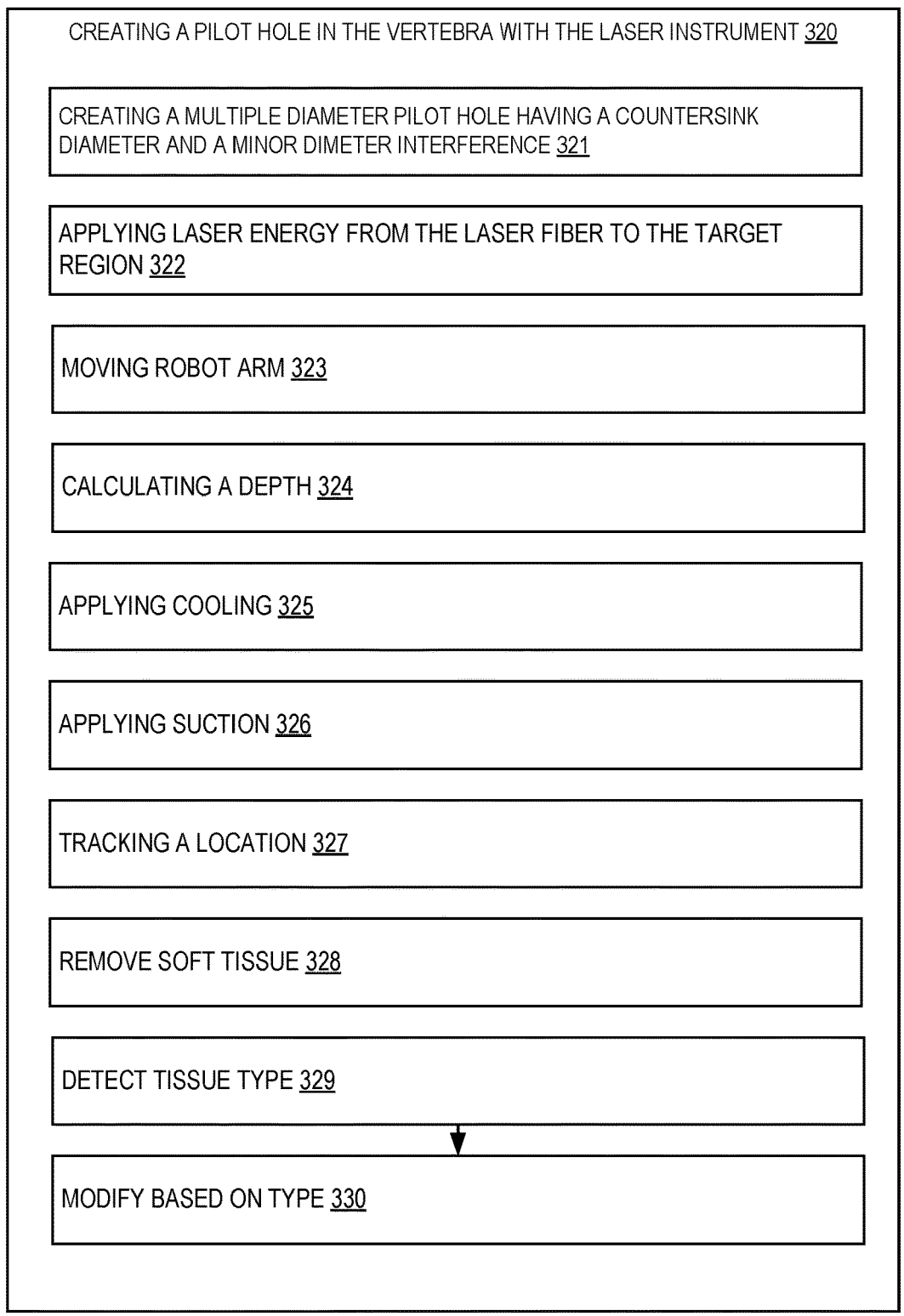

FIG. 3, which is made up of FIG. 3A and FIG. 3B, illustrates an example method 300 for performing spinal surgery using a laser. In an example implementation, one or more of the operations of method 300 are encoded in instructions executed by one or more processors for causing performance of the operations. The method 300 includes one or more operations, including operations 302-334. In the illustrated example, the method 300 begins with operation 302.

Operation 302 includes exposing a vertebra of a patient. The exposing can be achieved in any of a variety of ways, such as through percutaneous or open techniques. In an example, a surgeon or robot uses a tissue dilator to expose the vertebra 10 of the patient. The vertebra can be exposed via any of a variety of approaches, such as anterior, posterior, lateral or oblique. In the illustrated example, following operation 302 the flow of the method 300 moves to operation 304.

Operation 304 includes disposing a distal end 204 of a laser instrument 200 proximate the vertebra 10. In some examples, the laser instrument 200 is manually or automatically moved into position such that the distal end 204 of the laser instrument 200 is proximate the vertebra 10. In the illustrated example, following operation 304 the flow of the method 300 moves to operation 306.

Operation 306 includes conducting 306 a laser-based topographical analysis of the vertebra 10 using the laser instrument 200. In an example, the computer 120 causes the laser instrument 200 to emit a set of interrogation pulses 30 to a plurality of different locations proximate the vertebra 10. One or more of the interrogation pulses 30 are reflected back toward the distal end 204 of the laser instrument 200, which are collected and channeled back to the light detector 114. The received laser pulses 30 (e.g., as represented by data output from the light detector 114) are analyzed (e.g., to determine distances) and used to construct the laser-based topographical analysis. In an example, LIDAR (Light Detection and Ranging) techniques are applied. The resulting topographical analysis can be, for example, 3D representation of the structures interrogated by the interrogation pulses 30, such as the vertebra 10 and surrounding tissue. In the illustrated example, following operation 306 the flow of the method 300 moves to operation 310.

Operation 310 includes registering a patient's anatomy using the laser-based topographical analysis. For example, the laser-based topographical analysis is or is used to generate a model of the patient's anatomy, which is registered with one or more pre-operative or intraoperative scans (e.g., a preoperative 3D scan) of the patient's anatomy. In some examples, operation 310 includes operations 312 and 314. Operation 312 includes determining that the patient's spine shifted since a prior non-laser-based registration (e.g., preoperative or intra-operative CT scans). For example, the laser-based topographical analysis is compared to the prior non-laser based registration to determine an amount of difference. If the amount or quality of difference is sufficiently high (e.g., passes a threshold), then it can be determined that the patient's spine shifted since a prior non-laser-based registration. Operation 314 includes updating an existing non-laser-based registration using the laser-based topographical analysis. For example, the updating can include supplanting or correcting the existing registration with the data of the laser-based topographical analysis. In some examples, the laser-based registration is used to determine a confidence value in registration. For example, before or during the performance of the method 300, the patient's anatomy is registered using a non-laser registration technique to produce a non-laser registration. Then a registration confidence value for the registration is calculated using the laser-based topographical analysis. In the illustrated example, following operation 310 the flow of the method 300 moves to operation 320.

Operation 320 includes creating a pilot hole 12 in the vertebra 10 the laser instrument 200. In some examples, as shown in FIG. 3B, operation 320 includes operations 321-330.

Operation 321 includes creating a multiple diameter pilot hole 12 having a countersink diameter and a minor dimeter interference configured to improve pull out force and reduce insertion force of a screw to be disposed in the pilot hole 12.

Operation 322 includes applying laser energy from the laser instrument 200 to the target region. For example, the laser energy is applied in the form of laser pulses 20, 30. In an example, the laser energy or laser pulses are in a spectrum associated with Er:YAG. In an example, applying the laser energy includes applying the laser energy in a manner that is sub-ablative with respect to bone. In an example, applying the laser energy includes applying the laser energy in a manner that results in vaporizing water. The vaporization of water can cause the water to flash into steam and explodes, thereby disintegrating the surrounding bone.

Operation 323 includes moving the robot arm 132. For example, the position of the laser instrument 200 is controlled by the robot 130. Moving the robot arm 132 can include moving the robot arm 132 under a surgeon's control or automatically according to a plan. The robot arm 132 can move the laser instrument 200 to one or more positions for the application of the laser pulses 20, 30.

Operation 324 includes calculating a depth of the pilot hole 12. For example, the depth can be calculated using the laser instrument 200. For example, the laser instrument 200 can be controlled to emit one or more interrogation pulses 30, which are reflected off of tissue and detected by the light detector 114. The time from emission to detection of the interrogation pulses 30 can be used to determine the depth of the pilot hole 12. In some examples, the distance is modified based on a distance between the distal end of the laser instrument 200 and the start of the pilot hole 12 (e.g., as determined based on the navigation lumen 212 or the reference array 252).

Operation 325 includes applying cooling or irrigation. For example, the cooling is applied using a cooling lumen 216 of the laser instrument 200. In an example, the irrigator 116 pumps fluid from a fluid reservoir through the cooling lumen 216 such that the fluid is emitted proximate the distal end of the laser instrument 200 to cool a target area. In many examples, the target area being cooled is tissue proximate the area being cut. In other examples, the cooling is applied to one or more portions of the laser instrument 200.

Operation 326 includes applying suction. For example, the suction is applied using a suction lumen 218. For example, the suction generator 118 is activated and induces suction in the suction lumen 218 such that material proximate the distal end of the suction lumen 218 is evacuated through the suction lumen 218.

Operation 327 includes tracking a location, such as the location of the laser instrument 200 overall or the distal end 204 of the laser instrument 200. For example, the tracking is performed using the navigation lumen 212. In some examples, the tracking is achieved at least in part by the navigation system 190.

Operation 328 includes removing soft tissue. For example, the operation can include applying laser energy from the laser instrument 200 to remove soft tissue proximate the target region. In some examples, the parameters of the laser generator 112 are modified to improve the ability of the laser pulses 20 to remove the soft tissue. For example, the parameters can be modified to change a wavelength or intensity of the laser pulses 20.

Operation 329 includes detecting a tissue type. For example, the operation 329 includes detecting a tissue type of tissue to which the laser energy is to be applied. In an example, detecting the tissue type includes performing optical coherence tomography or performing spectroscopy. For example, the techniques can be performed by providing laser pulses 30 using the laser instrument 200 and detecting a response with the light detector 114. The response is analyzed using optical coherence tomography or spectroscopy principles. For example, an algorithm, lookup table, artificial intelligence, decision tree or other technique are applied to the results of the analysis to determine a corresponding tissue type. In some examples, following operation 329, the flow of the method 300 moves to operation 330.

Operation 330 includes modifying based on the detected tissue type. Operation 330 includes modifying a laser energy level based on the tissue type. For example, one or more parameters can be associated with the tissue type (e.g., in a lookup table or decision tree). The parameters are applied. In some examples, the modifying includes shutting off the laser generator, pausing a plan, moving the laser instrument 200, modifying the laser axis 208, or alerting a user (e.g., because the detected tissue type is contraindicated for treatment).

Returning to FIG. 3A, in the illustrated example, following operation 320 the flow of the method 300 moves to operation 332.

Operation 332 includes conducting a spectral analysis of laser reflection received through the laser instrument 200 to determine laser characteristics to be used to complete a surgical plan. For example, the analysis can be conducted using the computer 120 based on data produced by the light detector 114. The analysis can be used to determine that the surgical plan is complete (e.g., the expected tissue at the bottom of the pilot hole 12 is actually at the bottom of the pilot hole). In the illustrated example, following operation 332 the flow of the method 300 moves to operation 334.

Operation 334 includes placing a navigated instrument 170 or an implant 180 engaged with the navigated instrument 170 into the pilot hole 12. For example, the navigated instrument 170 or implant 180 is manually or automatically navigated into the pilot hole 12.

Second Example Method

Figure 4:
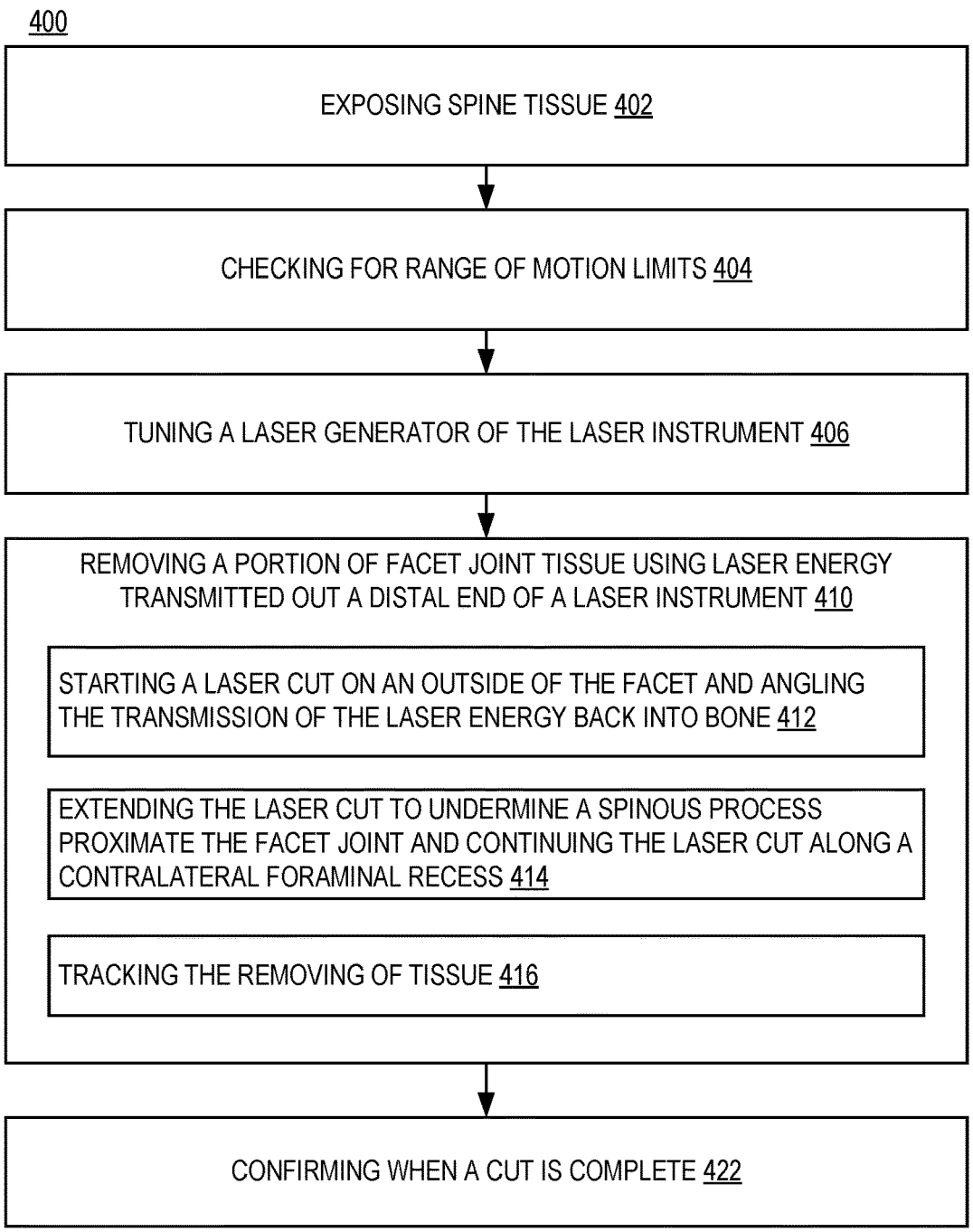
FIG. 4 illustrates a second method for removing a portion of facet joint tissue using laser energy.

FIG. 4 illustrates a second method 400 for removing a portion of facet joint tissue using laser energy. In the illustrated example, the method 400 begins with operation 402.

Operation 402 includes exposing spine tissue. For example, the operation 400 can include using minimally invasive or open access techniques. In an example, a tissue dilator is used to expose spine tissue, such as a vertebra 10. Following operation 402, the flow of the illustrated method 400 moves to operation 404.

Operation 404 includes checking for range of motion limits, such as range of motion limits for a robot arm 132 manipulating the laser instrument 200. Checking the range of motion limits can include determining whether the laser instrument 200 will be able to effectively treat target tissue given a current arrangement of the system 100 and patient. For example, range of motion limits can dictate a patient re-orientation or a different tip for the laser instrument 200 with more angulation. Following operation 404, the flow of the illustrated method 400 moves to operation 406.

Operation 406 includes tuning a laser generator 112 of the laser instrument 200. For example, the tuning can include tuning a laser generator 112 of the laser instrument 200 such that generated laser pulses 30 reach a frequency and intensity selected to cut a particular kind of tissue (e.g., facet joint tissue). Following operation 406, the flow of the illustrated method 400 moves to operation 410.

Operation 410 includes removing a portion of facet joint tissue using laser energy transmitted out a distal end of a laser instrument 200. For example, the operation can include applying laser pulses 20 generated by the laser generator 112 with the laser instrument 200 to treat the tissue of the facet joint. In some examples, the operation 410 includes one or more operations described above with respect to FIG. 3 with anatomical, tissue, and other references changed to reflect the removing facet joint tissue rather than, for example, forming a pilot hole 12 in a vertebra 10. In an example, the operation 410 includes operations 412, 414, and 416.

Operation 412 includes starting a laser cut on an outside of the facet and angling the transmission of the laser pulses 20 back into bone. For example, the angling can be achieved by using a light director 290 (e.g., a mirror or angled laser fiber) of the laser instrument 200 to perform the angling. The angle can be manually (e.g., by the surgeon) or automatically controlled. In further examples, the angling is achieved by changing a position of the laser instrument. The angling can include angling transmission of laser energy back into bone includes angling the transmission of laser energy in a direction other than toward disc tissue or nerve tissue.

Operation 414 includes extending the laser cut to undermine a spinous process proximate the facet joint and continuing the laser cut along a contralateral foraminal recess.

Operation 416 includes tracking the removing of tissue. For example, tracking the removal can include tracking the removing using laser topography, reflected laser energy, refracted laser energy, or optical coherence tomography to determine removed areas. For example, the tracking can include operations as described above in relation to FIG. 3, such as operation 324 (calculating a depth) and operation 329 (detect tissue type).

Following operation 410, the flow of the illustrated method 400 moves to operation 422.

Operation 422 includes confirming when a cut is complete. For example, the confirming can include using laser topography, laser reflection/refraction, or optical coherence tomography to confirm when a cut is complete. For example, laser topography can be used to generate a topographical map of the treated area that is analyzed (e.g., by an algorithm or surgeon) to determine whether the desired tissue was affected (e.g., removed). Laser reflection/refraction or optical coherence tomography can be used to determine the type of tissue present in a particular area. If a first tissue type is detected rather than a second tissue type, then it can be determined that the cut is completed because tissue of the first type was sufficiently removed.

Third Method

FIG. 5 illustrates a third example method 500 for creating a pilot hole 12 in a vertebra 10. In an example, the method 500 begins with operation 302.

Operation 302 includes exposing a vertebra 10 of a patient. In the illustrated example, following operation 302 the flow of the illustrated method 500 moves to operation 304.

Operation 304 includes disposing a distal end 204 of the laser instrument 200 proximate the vertebra 10. Following operation 304, the flow of the illustrated method 500 moves to operation 530.

Operation 530 includes creating a pilot hole 12 in the vertebra 10. In some examples, the operation 530 includes one or more aspects as described above in relation to operation 320 of FIG. 3. In the illustrated example, the operation 530 can further include operations 532 and 534.

Operation 532 includes advancing the laser instrument 200 toward the vertebra 10. For example, the laser instrument 200 is advanced toward the vertebra 10 after removing a first amount of tissue from the vertebra 10 and before removing a second amount of tissue from the vertebra 10. In some examples, the laser instrument 200 remains entirely outside of the pilot hole 12. In other examples, at least a portion of the laser instrument 200 enters the pilot hole 12.

Operation 534 includes repeatedly changing a direction of laser pulses 30 emitted from the laser instrument 200. In an example, changing the direction includes changing an angle of a light director 290 of the laser instrument 200. In another example, changing the direction includes changing an angle of a longitudinal axis 206 of the laser instrument 200 from a first angle to a second angle. For instance, the angle of the longitudinal axis 206 can be changed relative to a normal of the vertebra 10 or a center of the pilot hole 12. The changing of the direction can change the area of the tissue that is removed to form the pilot hole 12.

Following operation 530, the flow of the illustrated method 500 moves to operation 536.

Operation 536 includes measuring an impedance related to tissue defining a bottom of the pilot hole 12 to determine a tissue type. For example, the impedance can be measured to determine whether the tissue is bone. The measurement can be taken before, during, or after creating the pilot hole 12. The impedance can be optical impedance of a reflected laser pulse 30 detected by the light detector 114. The impedance can be analyzed to determine whether desired tissue has been removed and whether undesired tissue is present.

Fourth Method

Figure 6:
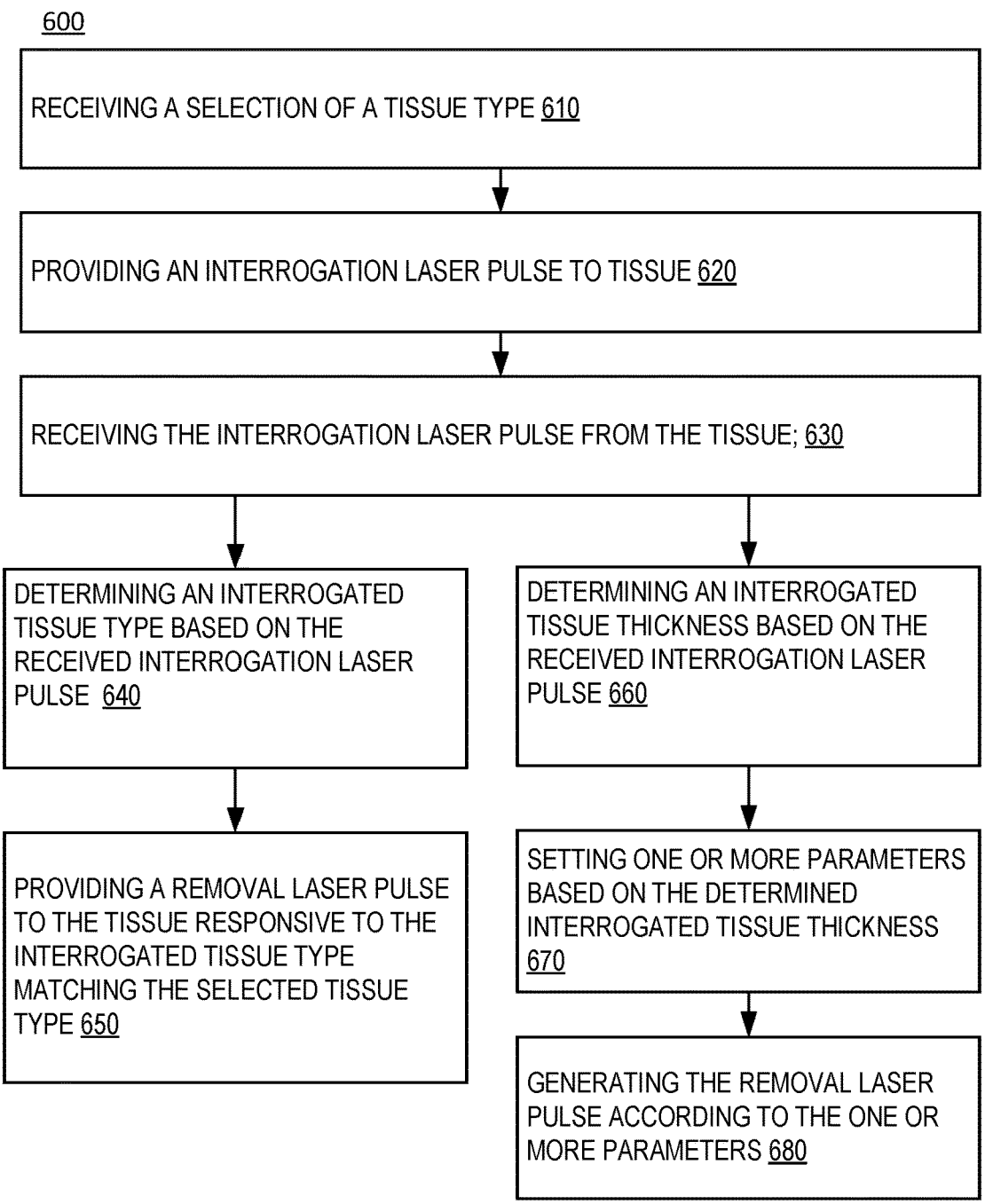
FIG. 6 illustrates a fourth example method for providing a removal laser pulse to tissue based on an interrogated tissue type.

FIG. 6 illustrates a fourth example method 600 for providing a removal laser pulse 20 to tissue based on an interrogated tissue type. In an example, the method 600 includes operations 610-680 and begins with operation 610.

Operation 610 includes receiving a selection of a tissue type, such as over a user interface 150 or from a file (e.g., surgical plan) or data structure defining the tissue type. For example, the tissue type can be a ligament tissue, disc tissue, tumor tissue, bone tissue, other types of tissue, or combinations thereof. The tissue type can be selected as part of creating a surgical plan for the patient. For example, the surgery can include the removal of disc tissue and the surgical planning process can include receiving a selection of a disc tissue type. Following operation 610, the flow of the illustrated method 600 moves to operation 620.

Operation 620 includes providing an interrogation laser pulse 30 to tissue. For example, the interrogation laser pulse 30 can be generated by the laser generator 112 using laser pulse generation parameters. The laser pulse generation parameters can be selected such that the interrogation laser pulse 30 does not substantially affect (e.g., ablate or remove) tissue in the way that the removal laser pulses 20 do. The interrogation laser pulse 30 parameters can be selected to generate a laser pulse 30 configured to be useful in the interrogation of tissue. The interrogation laser pulses 30 can be provided through the same or different optical channels (e.g., fibers) as the removal laser pulses 20. The interrogation laser pulses 30 can be generated using the same or different laser generator 112 as generates the removal laser pulses 20. One or more interrogation laser pulses 30 can be provided. Following operation 620, the flow of the illustrated method 600 moves to operation 630.

Operation 630 includes receiving the interrogation laser pulse 30 from the tissue. For example, the one or more interrogation laser pulses 30 generated in operation 620 are reflected or refracted by the tissue and eventually are conducted to the light detector 114, which receives the interrogation laser pulses 30. Following operation 630, the flow of the illustrated method 600 moves to one or both of operation 640 and operation 660.

Operation 640 includes determining an interrogated tissue type based on the received interrogation laser pulse 30. The received interrogation laser pulse 30 (e.g., as represented in the output of the light detector 114) can be analyzed using optical coherence tomography or spectroscopy principles. For example, an algorithm, lookup table, artificial intelligence, decision tree or other technique are applied to the results of the analysis to determine a corresponding tissue type. Following operation 640, the flow of the illustrated method 600 moves to operation 650.

Operation 650 includes providing a removal laser pulse 20 to the tissue responsive to the interrogated tissue type matching the selected tissue type. For example, this operation can result in providing the removal laser pulse 20 to remove tissue of a particular type while reducing the likelihood of removing tissue of another type.

In an example, responsive to the interrogated tissue type failing to match the selected tissue type, the removal laser pulse 20 is not provided and the aim of the laser instrument 200 is modified so a new area of tissue is targeted and the flow of the process can return to operation 620.

Operation 660 includes determining an interrogated tissue thickness based on the received interrogation laser pulse. For example, received interrogation laser pulse (e.g., as represented in output of the light detector 114) is analyzed using optical coherence tomography or spectroscopy principles. For example, an algorithm, lookup table, artificial intelligence, decision tree or other technique are applied to the results of the analysis to determine a thickness of the interrogated tissue. Following operation 660, the flow of the illustrated method 600 moves to operation 670.

Operation 670 includes setting one or more parameters based on the determined interrogated tissue thickness. For example, the parameters are parameters of the laser generator 112 and include, for example, laser pulse intensity and laser pulse wavelength. Following operation 670, the flow of the illustrated method 600 moves to operation 680.

Operation 680 includes generating the removal laser pulse according to the one or more parameters. For example, the operation can include operating the laser generator 112 with the one or more set parameters. The generated laser pulses 20 can be provided by the laser instrument 200 to treat patient tissue.

Fifth Method

Figure 7:
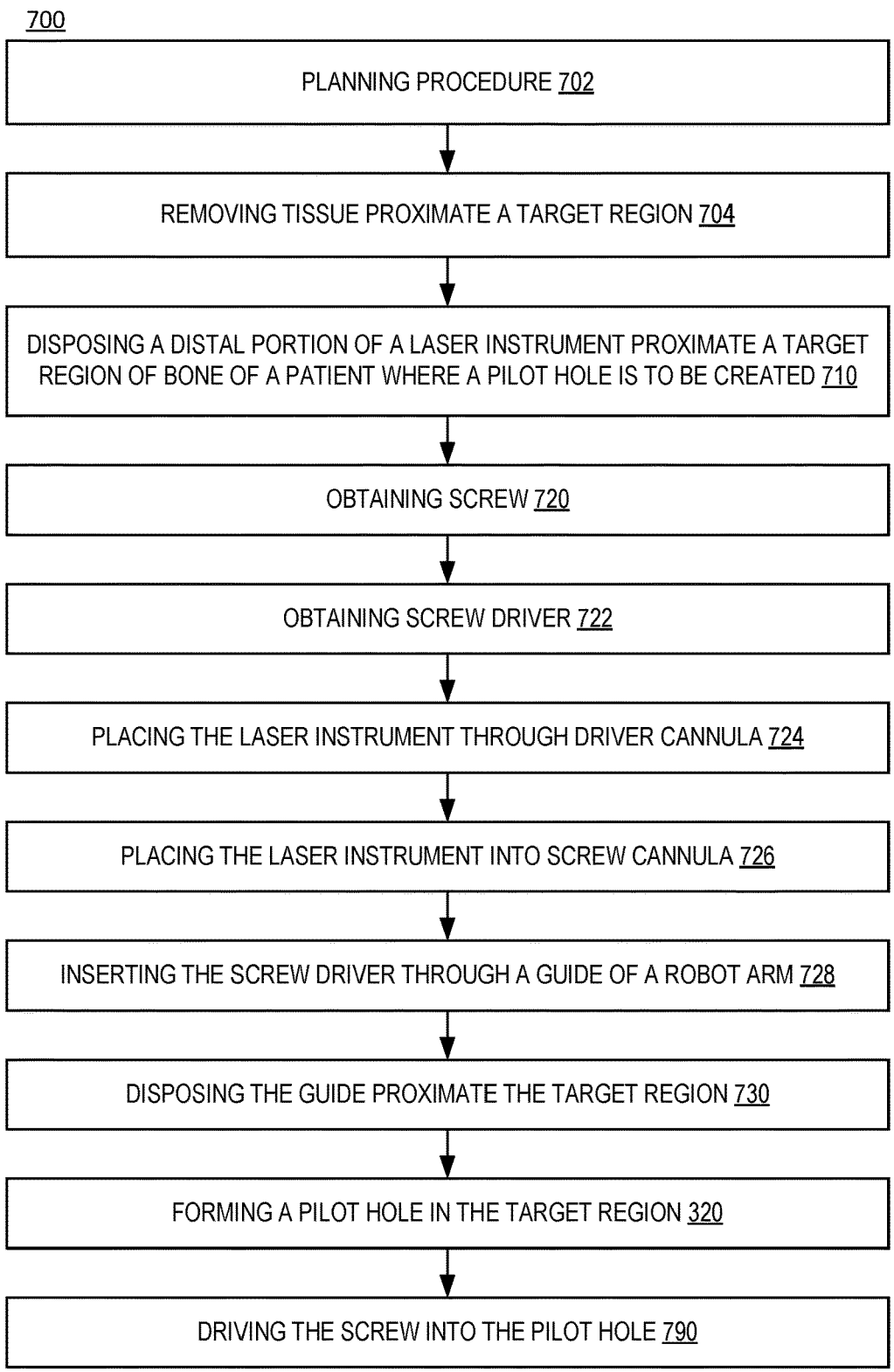
FIG. 7 illustrates a fifth example method for forming a pilot hole in a target region.

FIG. 7 illustrates a fifth example method 700 for forming a pilot hole 12 in a target region.

Operation 702 includes planning the procedure. For example, the operation 702 can include receiving an indication of the location of a target region. For example, the target region can be a region of a vertebra 10 at which the pilot hole 12 is to be formed. The operation 702 can include receiving one or more characteristics of a screw to be disposed in the pilot hole 12, such as the screw's length and diameter (e.g., shank diameter, thread diameter, and any taper of the screw). Planning the procedure can include determining a characteristic of the pilot hole 12 based on the one or more characteristics of the screw. For instance, a diameter and depth of the pilot hole 12 can be determined based on the diameter and length of the screw, respectively, using, for example predetermined lookup tables or algorithms. The computer 120 can perform one or more of the determinations and present the results on the user interface 150. The computer 120 can then receive confirmation of the determined characteristic of the pilot hole 12. Following operation 702, the flow of the illustrated method 700 moves to operation 704.

Operation 704 includes removing tissue proximate the target region. For example, a surgeon can remove tissue such that an instrument (e.g., a screw driver) can reach a starting point of a screw and a posterior cortex of a spinal vertebra. In an example, the tissue is removed using a laser, such as using one or more of the techniques described herein. Following operation 704, the flow of the illustrated method 700 moves to operation 710.

Operation 710 includes disposing a distal portion of the laser instrument 200 proximate a target region of bone of a patient where a pilot hole 12 is to be created. For example, the operation 710 can include automatically or manually moving the laser instrument 200 such that the distal end 204 of the laser instrument 200 is proximate the target region of the bone. Following operation 710, the flow of the illustrated method 700 moves to operation 720.

Operation 720 includes obtaining a screw, such as a screw having the characteristics selected during the planning operation 702. In an example, the screw is a cannulated screw, such as is described in more detail in FIG. 8. In some examples, the system 100 instructs a user to obtain the screw, such as providing a visual or audible output describing the screw. Following operation 702, the flow of the illustrated method 720 moves to operation 722.

Operation 722 includes obtaining a screw driver. In some examples, the system 100 instructs a user to obtain the screw, such as providing a visual or audible output describing the screw. The screw driver can be, for example, a cannulated manual or electric screw driver as is described in more detail in FIG. 8.

FIG. 8 illustrates an apparatus 800 including an example cannulated screw 810 and driver 820 with the laser instrument 200 inserted through the cannula. In particular, the illustrated example screw 810 is a fixed-axial pedicle bone screw. The screw 810 includes a screw proximal end 812 and a screw distal end 814. The proximal end 812 includes head 816 defining a tool opening 818 configured to receive any suitable driving tool tip 816 (e.g., compatible hex, flat, or Philips shapes). The distal end includes a threaded shank 822 configured to engage bone at a selected target site located inside the body of a patient (e.g. isthmus of the pedicle). At least a portion of the screw 810 is made from a surgically implantable material, such as titanium or stainless steel. The screw 810 includes a connector portion 824 fixedly connected to the head 816 portion of the screw 810. The connector portion 824 of the screw 810 is constructed and arranged to form a passageway designed to removably receive at least one biocompatible stabilizing member (e.g., an interconnecting rod or plate) and a set screw. The screw 810 defines a screw cannula 834 extending through the screw 810. The driver 820 can be a manual or automatic screw driver that defines a driver cannula 852. The driver cannula 852 is in communication with the screw cannula 834 when the screw 810 and driver 820 are coupled. In an example, the screw cannula 824 and the driver cannula 852 are configured (e.g., sized and shaped) to receive at least a portion of the laser instrument 200. As illustrated, the laser instrument 200 extends through both the screw cannula 824 and the driver cannula 852 such that the distal end 204 of the laser instrument 200 is proximate the distal portion 814 of the screw 810. In some examples, the laser instrument 200 is coaxial with the screw cannula 824. For instance, the diameter of the laser instrument 200 and the diameter of the screw cannula 824 can be sufficiently close in size that the laser instrument 200 can be slid through the screw cannula 824 while being relatively coaxially aligned with the screw cannula 824. In an example, the illustrated configuration is reached after completion operation 724 and operation 726.

Returning to FIG. 7, following operation 722, the flow of the illustrated method 700 moves to operation 724. Operation 724 includes placing the laser instrument 200 through the driver cannula 852 of the driver 820. For example, the distal end 204 of the laser instrument 200 is inserted through an opening of the driver 820 and into the driver cannula 852. Following operation 724, the flow of the illustrated method 700 moves to operation 726.

Operation 726 includes placing the laser instrument 200 into the screw cannula 824. For example, the laser instrument 200 is placed into the screw cannula 824 such that the distal end 204 of the laser instrument 200 is proximate the screw distal end 814. In some examples, the operation 724 and operation 726 are performed while the screw 810 and the driver 820 are coupled. Following operation 726, the flow of the illustrated method 700 moves to operation 728.

Operation 728 includes inserting the screw driver 820 through a guide 136 of a robot arm 132. For example, the resulting arrangement can be as is shown in FIG. 1, for example, with instrument 170 corresponding to the driver 820 and implant 180 corresponding to the screw 810. The guide 136 can constrain the movement of the screw driver 820 and screw 810 to facilitate accurate placement of the screw 810 and accurate use of the laser instrument 200. Following operation 728, the flow of the illustrated method 700 moves to operation 730.

Operation 730 includes disposing the guide 136 proximate the target region. For example, the guide 136 is so disposed using the robot arm 132 to move the guide 136 into position. In some examples, the robot arm 132 is moved automatically (e.g., following a plan) or manually (e.g., at the manual direction of a surgeon). Following operation 702, the flow of the illustrated method 700 moves to operation 320.

Operation 320 includes forming a pilot hole 12 in the target region and is described in more detail in relation to FIG. 3. The pilot hole 12 can be formed using the laser instrument 200 while the laser instrument 200 disposed in the cannulated screw. Following operation 320, the flow of the illustrated method 700 moves to operation 790.

Operation 790 includes driving the screw 810 into the pilot hole 12 using the driver 820.

Sixth Method

Figure 9:
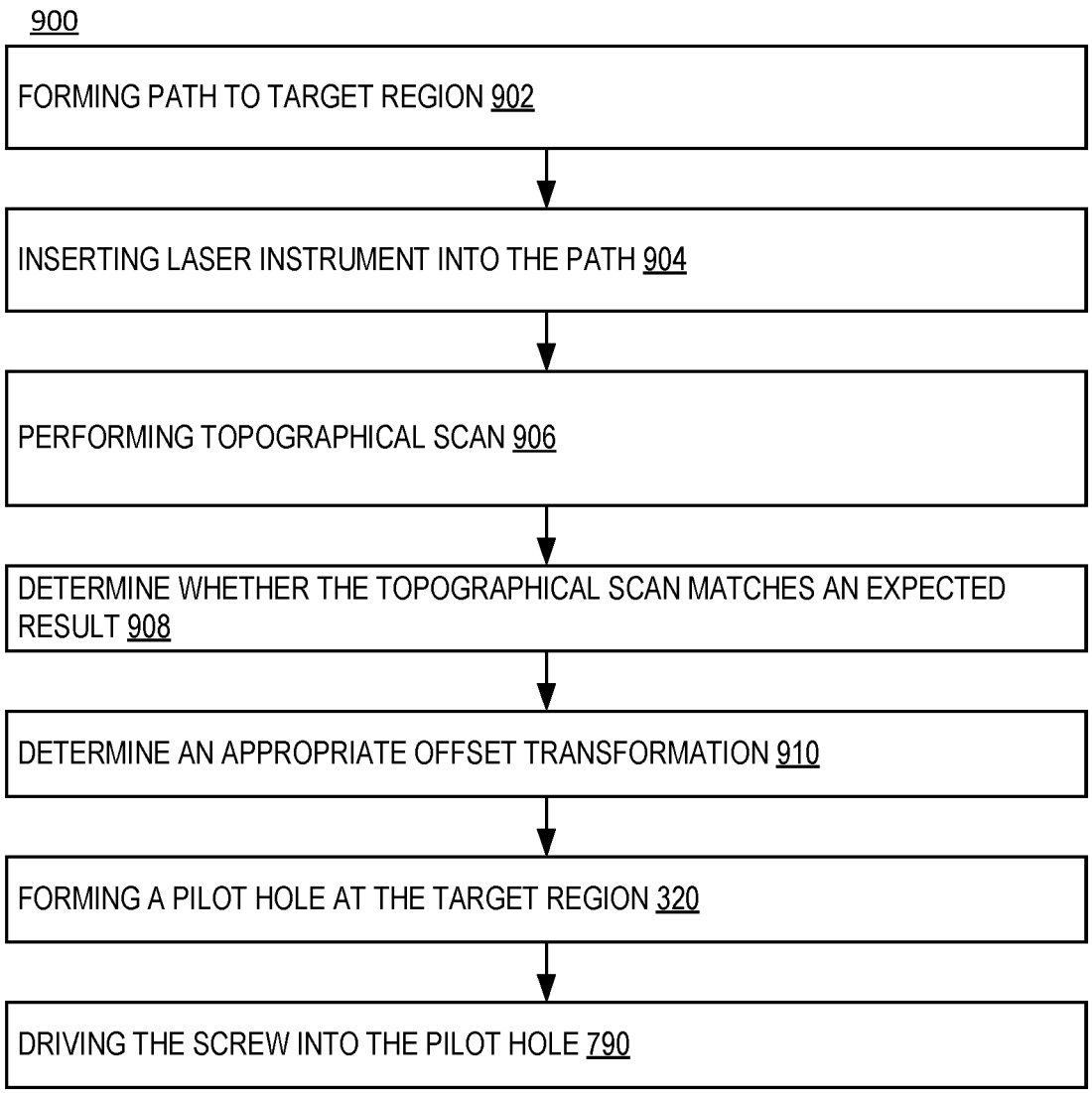
FIG. 9 illustrates a sixth method for forming a pilot hole at the target region.

FIG. 9 illustrates a sixth method 900 for forming a pilot hole 12 at a target region.

Operation 902 includes forming a path to a target region. For example, the operation 902 can include forming a percutaneous path through tissue to a target region of a vertebra 10. In some examples, the path includes forming a path using minimally-invasive surgical techniques or via open surgical techniques. Following operation 902, the flow of the illustrated method 900 moves to operation 904.

Operation 904 includes inserting the laser instrument 200 into the path. For example, the operation 904 includes inserting a laser instrument 200 into the percutaneous path such that a distal end 204 of the laser instrument 200 is disposed proximate the target region. In an example, the distal end 204 of the laser instrument 200 is disposed in a region that would be inaccessible but for the path being formed (e.g., the distal end is within the patient). Following operation 904, the flow of the illustrated method 900 moves to operation 906

Operation 906 includes performing a topographical scan. For example, the operation 906 can include one or more techniques described above in relation to operation 310 of FIG. 3. Following operation 906, the flow of the illustrated method 900 moves to operation 908.

Operation 908 includes determining whether the topographical scan matches an expected result. In an example, the expected result is an expected model of the patient's anatomy generated using pre-operative or intra-operative medical imaging. To determine whether there is a match, the laser-based topographical analysis is compared to the expected result. If the amount or quality of difference is sufficiently high (e.g., passes a threshold), then it can be determined that there is not a match. Following operation 908, the flow of the illustrated method 900 moves to operation 910

Operation 910 includes determining an appropriate offset transformation. Determining the offset transformation can include determining an offset transformation sufficient to align the topographical scan with the expected result. In at least some examples, the operation 910 includes one or more aspects described above in relation to operation 314. Following operation 910, the flow of the illustrated method 900 moves to operation 320.

Operation 320 includes forming a pilot hole 12 at the target region. In some examples, rather than being formed with a laser, the pilot hole 12 is formed using traditional techniques. Following operation 320, the flow of the illustrated method 900 moves to operation 790.

Operation 790 includes driving the screw into the pilot hole.

Computing Environment

FIG. 10 illustrates an example computing environment 1000 with which techniques described herein can be implemented. The computing environment 1000 is a set of one or more virtual or physical computers configured to cause output based on data. In many examples, the computing environment 1000 is a workstation, desktop computer, laptop computer, or server. In other examples, the computing environment 1000 is a virtual machine, group of computers, or other computing environments.

In the illustrated example, the computing environment 1000 includes one or more processors 1010, memory 1020, and an interface 1030 coupled to a network 1002. The network 1002 is a group of communicatively coupled computing environments and associated hardware, such as a local area network, the Internet, other networks, or combinations thereof.

The one or more processors 1010 are one or more physical or virtual components configured to obtain and execute instructions. In many examples, the one or more processors 1010 are central processing units, but can take other forms such as microcontrollers, microprocessors, graphics processing units, tensor processing units, other processors, or combinations thereof.

The memory 1020 is one or more physical or virtual components configured to store information, such as data or instructions. In some examples, the memory 1020 includes the computing environment's main memory (e.g., random access memory) or long-term storage memory (e.g., a solid state drive). The memory can be transitory or non-transitory computer-readable or processor-readable storage media.

The interface 1030 is a set of one or more components by which the computing environment 1000 can provide output or receive input. For example, the interface 1030 can include one or more user input components, such as one or more sensors, buttons, pointers, keyboards, mice, gesture controls, touch controls (e.g., touch-sensitive strips or touch screens), eye trackers, voice recognition controls (e.g., microphones coupled to appropriate natural language processing components), other user input components, or combinations thereof. The interface 1030 can include one or more user output components, such as one or more lights, displays, speakers, haptic feedback components, other user output components, or combinations thereof. The interface 1030 can further include one or more components configured to provide output to or receive input from other devices, such as one or more ports (e.g., USB ports, THUNDERBOLT ports, serial ports, parallel ports, Ethernet ports) or wireless communication components (e.g., components configured to communicate according to one or more radiofrequency protocols, such as WI-FI, BLUETOOTH, ZIGBEE, or other protocols).

The computing environment 1000 can include one or more additional components or connections among components (e.g., busses).

The computing environment 1000 can be configured to implement one or more aspects described herein. Algorithms, steps, or procedures for so configuring the computing environment and performing functions described herein can be understood from the description herein in view of knowledge in the art of how to implement computer functions.

Example techniques for implementing such computer functions include frameworks and technologies offering a full stack of plug-and-play capabilities for implementing desktop and browser-based applications (e.g., the applications implementing aspects described herein). The frameworks can provide desktop web application featuring or using an HTTP server such as NODEJ or KATANA and an embeddable web browser control such as the CHROMIUM EMBEDDED FRAMEWORK or the JAVA/.NET CORE web view. The client-side frameworks can extend that concept by adding plug-and-play capabilities to desktop and the web shells for providing apps capable of running both on the desktop and as a web application. One or more components can be implemented using a set of OWIN (Open Web Interface for .NET) components built by MICROSOFT targeting the traditional .NET runtime. KATANA, and by definition OWIN, allow for chaining together middleware (OWIN-compliant modules) into a pipeline thus offering a modular approach to building web server middleware. For instance, the client-side frameworks can use a Katana pipeline featuring modules such as SIGNALR. The plug-and-play capabilities can provide a framework allowing runtime assembly of apps from available plugins. An app built atop of a plug-and-play framework can have dozens of plugins, with some offering infrastructure-level functionality and other offering domain-specific functionality. The CHROMIUM EMBEDDED FRAMEWORK is an open source framework for embedding the CHROMIUM browser engine with bindings for different languages, such as C #or JAVA. OWIN is a standard for an interface between .NET web applications and web servers aiming at decoupling the relationship between ASP.NET applications and IIS by defining a standard interface.

Further example techniques for implementing such computer functions include frameworks and technologies provided by or in conjunction with programming languages and associated libraries. For example, languages such as C, C++, C#, PYTHON, JAVA, JAVASCRIPT, RUST, assembly, HASKELL, other languages, or combinations thereof can be used. Such languages can include or be associated with one or more standard libraries or community provided libraries. Such libraries in the hands of someone skilled in the art can facilitate the creation of software based on descriptions herein, including the receiving, processing, providing, and presenting of data. Example libraries for PYTHON and C++ include OPENCV (e.g., which can be used to implement computer vision and image processing techniques), TENSORFLOW (e.g., which can be used to implement machine learning and artificial intelligence techniques), and GTK (e.g., which can be used to implement user interface elements). Further examples include NUMPY for PYTHON (e.g., which can be used to implement data processing techniques). In addition, other software can provide application programming interfaces that can be interacted with to implement one or more aspects described herein. For example, an operating system for the computing environment (e.g., WINDOWS by MICROSOFT CORP., MACOS by APPLE INC., or a LINUX-based operating system such as UBUNTU by CANONICAL LTD.) or another component herein (e.g., an operating system of the robot 130, such as IIQKA.OS or SUNRISE.OS by KUKA ROBOTICS CORPORATION where the robot 130 is a model of KUKA ROBOTICS CORPORATION) can provide application programming interfaces or libraries to usable to implement aspects described herein. As a further example, a provider of the navigation system 190, laser console 110, or another component may not only provide hardware components (e.g., a camera or laser generator), but also software components (e.g., libraries, drivers, or applications) usable to implement features with respect to the component.

Implant Shaping

Figure 11:
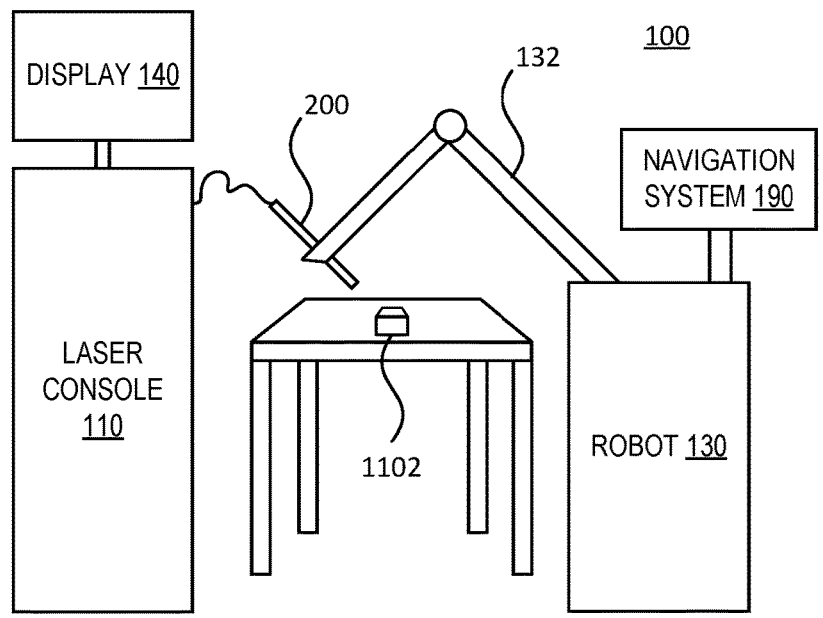
FIG. 11 illustrates the system being used to shape an implant blank into a customized implant.

FIG. 11 illustrates the system 100 being used to shape an implant blank 1102 into a customized implant. While disclosed examples have been described above in the context of modifying patient tissue, disclosed technology can be used to intraoperatively modify implants for implantation in the patient. In an example, a laser is used to shape an implant. Once confident that implant sizing is correct (e.g. using expandable trials, static trials), an implant blank would be placed in the working area of the surgical laser. The preoperative implant design could be used or modified in the operating room. The laser would then cut/sculpt the implant blank to match the required geometry.

Figure 12:
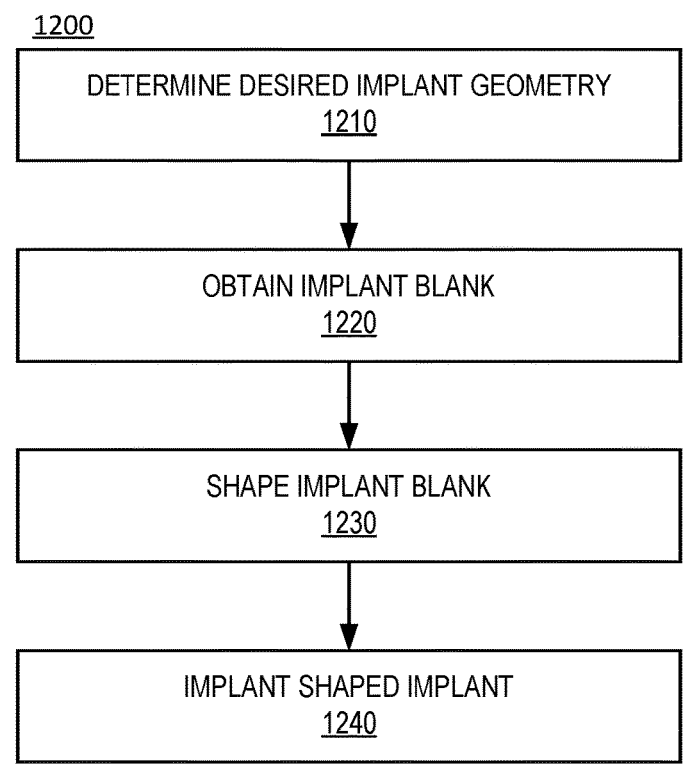
FIG. 12 illustrates an example method of forming an implant with the laser.

FIG. 12 illustrates an example method 1200 of forming an implant with the laser 200. One or more of the operations can be performed preoperatively or intraoperatively. One or more of the operations can be performed before, during, or after one or more of the operations described elsewhere herein. The method 1200 can begin with operation 1210.

Operation 1210 includes determining desired implant geometry. The desired implant geometry can be determined in any of a variety of ways. In some examples, the desired implant geometry can be the size of the implant (e.g., anterior-posterior size, medial-lateral size), shape of the implant (e.g., contours of the sides, faces of the implant, or angle of the implant), and surface characteristics of the implant (e.g., retention features, surface roughening, or other characteristics). The shape of the implant can be selected or determined to achieve a desired correction (e.g., sagittal or coronal balance). The desired geometry can be obtained via user input (e.g., the surgeon may determine such information based on intraoperative trial sizes). In addition or instead, the desired geometry can be determined based on analysis of one or more preoperative or intraoperative images. For example, implant height or angle can be selected to achieve a desired surgical outcome (e.g., using a planning platform such as IGA by NUVASIVE). Desired implant shape can be determined from endplate topology of the patient's vertebral anatomy, such as from preoperative or intraoperative imaging or from scanning with the laser 200. Example techniques for determining vertebral body endplate shape and size is disclosed in US 2020/0320786, filed Apr. 19, 2020, which is hereby incorporated herein by reference in its entirety for any and all purposes. The desired shape of the implant can be determined based on a shape that would complement the shape of the endplates. Following operation 1210, the flow of the method 1200 can move to operation 1220.

Operation 1220 can include obtaining the implant blank 1102. The implant blank 1102 can be a surgical interbody implant from a material cuttable by the laser 200. In an example, the implant blank 1102 is constructed from a plastic (e.g., PEEK), a metal, or bone material (e.g., allograft or autograft). Beneficially, the implant blank 1102 can be a bone material that the laser 200 can effectively cut (e.g., the same laser 200 can be used to cut the implant blank 1102 as used to cut the bony material of the patient).

In an example, the implant blank 1102 is obtained from an autograft harvest site of the patient. The robot 130 can control the laser 200 to cut bone from an autograft harvest site of the patient (e.g., at the patient's iliac crest or near the surgical site). The bone can be removed in a shape corresponding to the implant geometry. Following operation 1220, the flow of the method 1200 can move to operation 1230.

Operation 1230 includes shaping the implant blank 1102 with the laser 200. For example, the robot 130 can move the laser 200 and the laser 200 can be activated to shape the implant blank 1102. The operation 1230 can include registering the geometry of the implant blank 1102, such as with laser-based topographical analysis, a camera system, or the navigation system 190. The registration can be performed with any of the techniques described herein. In addition or instead, the shaping of the implant blank 1102 can be performed using one or more CNC (Computer Numerical Control) or CAM (Computer Aided Manufacturing) techniques running on the laser console 110, the robot 130, another system, or combinations thereof. The operation 1230 can be performed intraoperatively, such as while an incision is open in the patient, while the patient is anesthetized, or while the patient is in an operating room. Following operation 1230, the flow of the method can move to operation 1240.

Operation 1240 includes implanting the shaped implant in the patient.

Ultrasonic Cutting

Figure 13:
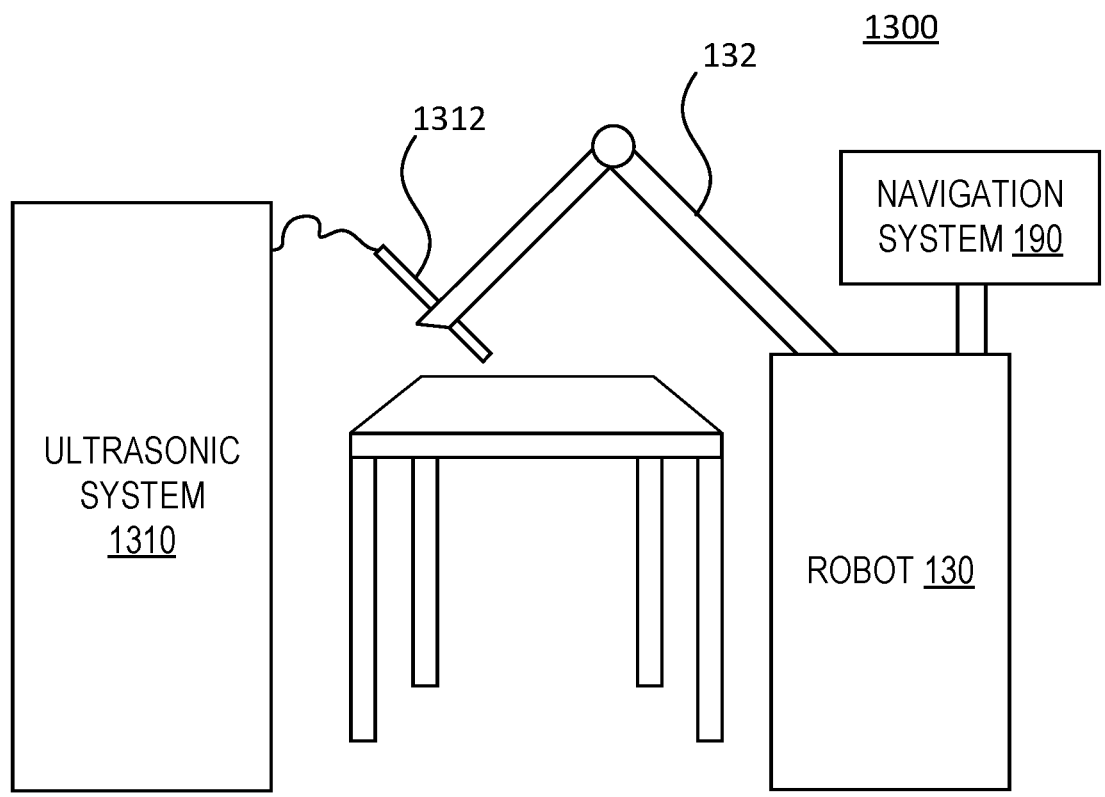
FIG. 13 illustrates an example ultrasonic cutting system.

While many examples herein were described in relation to lasers, examples can be modified to use other kinds of cutting tools, such as ultrasonic cutting tools. For example, the operations of methods 400 and 700 can be modified to use an ultrasonic cutting system rather than a laser. An example system 1300 for ultrasonic cutting is shown in FIG. 13. As illustrated, the system 1300 includes an ultrasonic cutting system 1310, an ultrasonic cutting probe 1312, a robot 130 having a robot arm 132 holding the ultrasonic cutting probe 1312, and a surgical navigation system 190.

The ultrasonic cutting system 1310 and the ultrasonic cutting probe 1312 can take any of a variety of different forms. There are various kinds of ultrasonic cutting systems 1310 and probes 1312 known in the art for modifying or ablating tissue. For example, U.S. Pat. No. 6,361,531, which is hereby incorporated herein by reference in its entirety for any and all purposes, shows and describes an ultrasonic cutting tissue treatment system and itself references many patents describing ultrasonic cutting systems. This patent is hereby incorporated herein by reference in its entirety for any and all purposes.

In one such example, ultrasonic ablation or ultrasonic cutting can be used to create a pilot hole. The ultrasonic cutting ablation probe 1312 can be advanced through a driver cannula 852 of a screw driver and through a screw cannula 834 of a screw 810. The robot arm 132, can hold a trajectory of a screw driver while the ultrasonic probe 1312 is disposed sufficiently proximate the distal end of the screw for the probe 1312 to affect tissue and allow for the screw to follow. Beneficially, the probe 1312 can affect tissue to facilitate forming the pilot hole even when the slippery curves of bone would have resisted the screw starting in a desired trajectory originally. If the user goes freehand then they can focus on the monitor to hold the desired trajectory and then gradually advance the ultrasonic ablation probe along the desired trajectory without having to look at their hands as there is not real force required or significant hand eye coordination. They can observe the probes progress and then when it has reached the through the pedicle safely entering the vertebral body have the screw follow along without having to watch the monitor since the trajectory is established. The ability to do this as one progressive step not only reduces operative time it preserves the ideal trajectory with or without a robot.

Beneficially, the ultrasonic cutting ablation probe 1312 need not require a physical impact or rotation which induce skiving as they create a pilot hole in the pedicle. Use with a navigated robot to hold the trajectory onto the plan even when the patient moves and the low force required to ablate tissue would allow it to stay along the planned trajectory. The screw would follow the shaft of the ultrasonic cutting ablation probe 1312 to resist the screw from skiving off of the bone. This technique can be integrated with Neuromonitoring EMG or bipolar impedance to confirm there are no nerves in the way or we accidentally break out of the pedicle.

Creating Window

In some examples, the laser or another cutting apparatus is used to form a window in a vertebral body for decompression. For instance, cervical decompression can be performed. Decompression of the spinal cord or other nerve tissue may be beneficial and that decompression needs to occur directly posterior to the vertebral body. Such a use is shown and described in relation to FIGS. 14 and 15.

Figure 14:
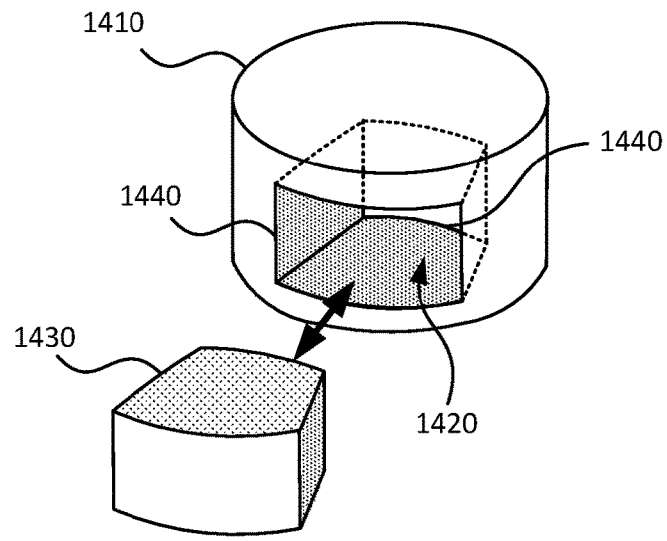
FIG. 14 illustrates a vertebral body having a window cut therein about a border.

FIG. 14 illustrates a vertebral body 1410 having a window 1420 cut therein about a border 1440. A boney plug 1430 removed from the window 1420 is shown proximate the window 1420. The window 1420 can be formed in an anterior face of the vertebral body 1410. As illustrated, the window 1420 is a cut through the entire vertebral body 1410 (e.g., from an anterior face of the vertebral body to a posterior face of the vertebral body, such as the vertebral foramen). In an example, the window 1420 has a taper such that a border 1440 on one face has a larger perimeter than a border 1440 on another face of the vertebral body 1410.

Figure 15:
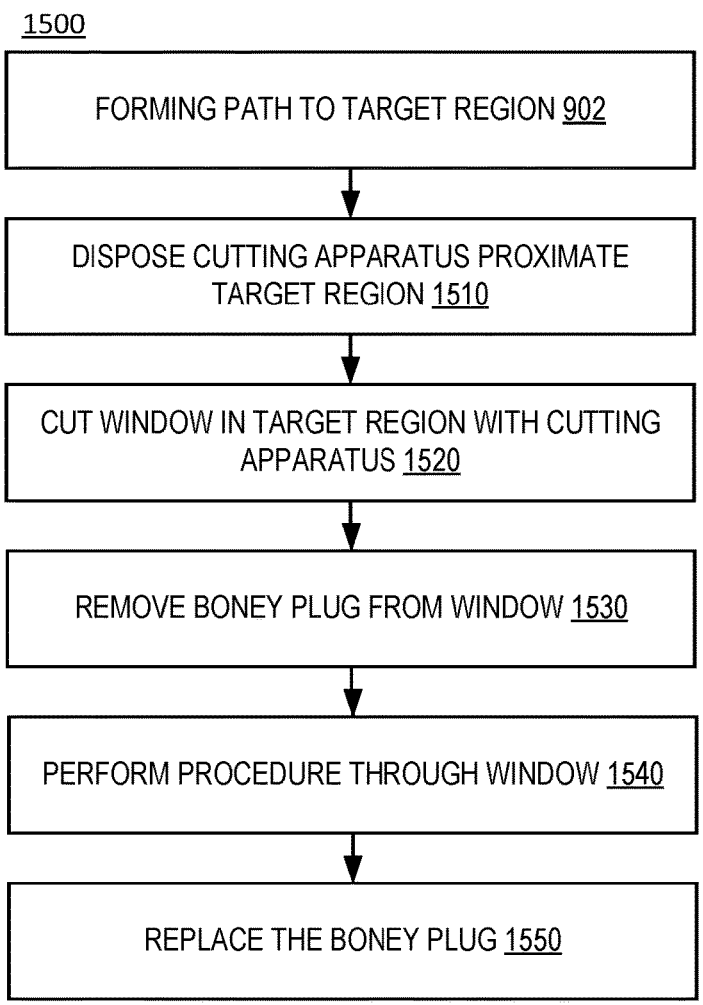
FIG. 15 illustrates a method for forming a window and performing a procedure through the window.

FIG. 15 illustrates a method 1500 for forming a window and performing a procedure through the window. The method 1500 begins with operation 902, which includes forming a path to a target region (e.g., a patient's vertebra having the vertebral body 1410). Operation 902 is described in more detail above. In some examples, the accessing can be performed via an anterior path to the vertebral body 1410. Following operation 902, the flow of the method 1500 moves to operation 1510.

Operation 1510 includes disposing a cutting apparatus proximate the target region. The cutting apparatus can take any of a variety of forms, such as the laser instrument 170 or the ultrasonic cutting probe 1312 held by the robot 130. Before, during, or after this operation 1510, the cutting apparatus can be registered to the spine. The cutting apparatus can be sufficiently proximate so the cutting apparatus can be used as described in operation 1520. Following operation 1510, the flow of the method 1400 can move to operation 1520.

Operation 1520 includes cutting a window in the target region with the cutting apparatus. The cutting apparatus can be used to cut a window 1420 in the target region, such as a vertebral body 1410. In an example, the size and shape of the window 1420 in the vertebral body can be planned preoperatively. Where the cutting apparatus is a laser, the laser can be tuned to cut bone rather than soft tissue. The cutting can include guiding the cutting apparatus with the robot 130 to cut a border 1440 around the window 1420, resulting in a boney plug 1430 within the window 1420. In some examples, the cutting can occur such that the boney plug 1430 has a proximal to distal taper. The taper can be such that depth of the boney plug 1430 can be controlled when the boney plug 1430 is placed back in the window 1420. Following operation 1520, the flow of the method 1500 can move to operation 1530.

Operation 1530 includes removing the boney plug 1430 from the window 1420. For example, the boney plug 1430 can be pulled manually or with the benefit of a tool. Once removed the boney plug 1430 can be retained for later use.

Operation 1540 includes performing a procedure through the window 1420. In an example, the procedure is decompression of nerve tissue. For example, an instrument (e.g., a curved drill) is inserted through the window and used to decompress the posterior vertebral body and ligaments. In some examples, the operation 1540 includes placing an implant through or within the window 1420. Following operation 1540, the flow of the method 1500 moves to operation 1550.

Operation 1550 includes replacing the boney plug 1430 in the window 1420.

While the above has been described with respect to forming a window in a vertebral body, in other examples, the above technique can be applied to other structures. For example, during certain lateral spinal fusion procedures a surgeon may want to access an L4-L5 or L5-S1 disc space of a patient, but accessing that space laterally may be difficult or impossible due to the patient's iliac crest blocking access. The above technique can include using the cutting apparatus to cut a window or notch within the iliac crest to form a window through which a lateral interbody fusion can be performed. The size and shape of the window can be programmed either pre-operatively or intraoperatively over the area desired. The shape of this window can be optimized to minimize the size of the access needed and customized to best fit any additional retraction instruments needed. The window is cut in the bone and the bone plug is retained for future replacement or can be used for graft material.

References herein "embodiments", "examples", "implementations", or the like indicate that the thing described may include one or more particular features, structures, components, aspects, relationships, or characteristics. But such recitations do not necessarily mean that all of the particular features, structures, components, aspects, relationships, or characteristics are required, necessary, or essential. Further, features, structures, components, aspects, relationships, or characteristics can be used with other embodiments, examples, implementations and the like, whether or not explicitly described unless expressly stated to the contrary.

While various descriptions of the aspects of the present disclosure may refer to a surgeon, or surgeons, it is to be understood that the functionality of such aspects may extend to other users, as contextually appropriate, such that the term "surgeon" supports the term "user". In some examples, a surgeon can be a surgical robot.

Examples herein include methods that include operations. Although the operations in each figure are illustrated in a sequential order, the operations may in some instances be performed in parallel, and/or in a different order than those described therein. Also, the various operations may be combined into fewer operations, divided into additional operations, and/or removed based upon the desired implementation.

In addition, diagrams can show the functionality of possible implementations. Operations can represent a module, a segment, or a portion of program code, which includes one or more instructions executable by one or more processors (e.g., CPUs) for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or random access memory, and/or persistent long term storage, such as read only memory, optical or magnetic disks, or compact-disc read only memory, for example. The computer readable media may be able, or include, any other volatile or non-volatile storage systems. The computer readable medium may be considered a computer readable storage medium, a tangible storage device, or other article of manufacture, for example. The computer-readable medium can be communicatively coupled to the one or more processors. The one or more processors can be coupled to one or more interfaces for providing data to or receiving data from one or more users or other devices. Example interfaces include universal serial busses, displays, speakers, buttons, networking components (e.g., wired or wireless networking components), other interfaces, or combinations thereof).

Operations can represent circuitry that is wired to perform the specific logical functions in the process. Illustrative methods can be carried out in whole in or in part by a component or components in the cloud and in a system. However, it should be understood that the example methods may instead be carried out by other entities or combinations of entities (e.g., by other computing devices and/or combination of computer devices), without departing from the scope of the invention. For example, certain operations can be fully performed by a computing device (or components of a computing device such as one or more processors), or can be distributed across multiple components of the computing device, across multiple computing devices, and/or across a server.

We claim:

1. A method for performing spinal surgery, the method comprising:
    exposing a vertebra of a patient;
    disposing a distal end of a laser instrument proximate the vertebra;
    conducting a laser-based topographical analysis of the vertebra using the laser instrument;
    registering a patient's anatomy using the laser-based topographical analysis; and
    creating a pilot hole in the vertebra with the laser instrument,
    wherein creating a pilot hole in the vertebra with the laser instrument includes creating a multi-diameter pilot hole.

2. The method of claim 1, further comprising:
    determining that the patient's spine shifted since a prior non-laser-based registration; and
    wherein the registering of the patient's anatomy includes:
        updating an existing non-laser-based registration using the laser-based topographical analysis.

3. The method of claim 1, wherein creating the multi-diameter pilot hole includes:

creating a multiple diameter pilot hole having a countersink diameter and a minor dimeter interference.

4. The method of claim 1, further comprising:
placing a navigated instrument or an implant engaged with the navigated instrument into the pilot hole.

5. The method of claim 1, further comprising:
conducting a spectral analysis of laser reflection received through the laser instrument to determine laser characteristics to be used to complete a surgical plan.

6. The method of claim 1, further comprising:
registering a patient's anatomy using a non-laser registration technique to produce a non-laser registration;
conducting a laser-based topographical analysis of the vertebra; and
calculating a registration confidence value for the registration using the laser-based topographical analysis.

7. A method comprising:
identifying range of motion limits;
selecting a tip for a laser instrument based on an angulation of the tip and the range of motion limits; and
removing a portion of facet joint tissue of a of a facet of a vertebra using laser energy transmitted from a distal end of the tip of the laser instrument,
wherein the removing includes starting a laser cut on an outside of the facet and angling the transmission of the laser energy back into bone.

8. The method of claim 7,
wherein the laser instrument comprises an elongate shaft that defines a longitudinal axis;
wherein the laser instrument defines a laser pulse axis along which the laser instrument is configured to direct laser pulses; and
wherein the laser pulse axis is non-parallel with respect to the longitudinal axis.

9. The method of claim 7, further comprising: using a tissue dilator to expose spine tissue.

10. The method of claim 7, further comprising: using laser topography, laser reflection, laser refraction, or optical coherence tomography to confirm when a cut is complete.

11. The method of claim 7, wherein starting the laser cut on an outside of the facet and angling the transmission of laser energy back into bone includes using a mirror or angled laser fiber to perform the angling.

12. The method of claim 7, wherein starting the laser cut on an outside of the facet and angling the transmission of laser energy back into bone includes angling the transmission of laser energy in a direction other than toward a disc or nerve.

13. The method of claim 7, further comprising: extending the laser cut to undermine a spinous process proximate the facet joint and continuing the laser cut along a contralateral foraminal recess.

14. The method of claim 7, further comprising: checking for range of motion limits that may dictate a patient reorientation.

15. The method of claim 7, further comprising tuning a laser generator of the laser instrument such that generated laser pulses reach a frequency selected to cut a particular kind of tissue.

16. The method of claim 7, further comprising tracking the removing through laser topography, reflected laser energy, refracted laser energy, or optical coherence tomography to determine removed areas.

17. A method comprising:
exposing a vertebra of a patient;
disposing a distal portion of a laser instrument proximate the vertebra; and
creating a pilot hole in the vertebra, wherein the creating of the pilot hole includes, while creating the pilot hole, repeatedly changing a direction of laser pulses emitted from the laser instrument.

18. The method of claim 17, wherein changing the direction of the laser pulses emitted from the laser instrument includes:
changing an angle at which laser pulses leave the laser instrument by changing an angle of a light director of the laser instrument; or
changing an angle of a longitudinal axis of the laser instrument from a first angle to a second angle.

19. The method of claim 17,
wherein creating the pilot hole includes:
advancing the laser instrument toward the vertebra after removing a first amount of tissue from the vertebra and before removing a second amount of tissue from the vertebra; and
after creating the pilot hole, measuring an impedance related to tissue defining a bottom of the pilot hole to determine whether the tissue is bone.

* * * * *